US010668058B2

(12) United States Patent
Rose et al.

(10) Patent No.: US 10,668,058 B2
(45) Date of Patent: Jun. 2, 2020

(54) DEVICE AND METHOD FOR DELIVERY OF A MEDICAMENT

(75) Inventors: Jed E. Rose, Durham, NC (US); Seth D. Rose, Tempe, AZ (US); James Edward Turner, Homewood, IL (US); Thangaraju Murugesan, Durham, NC (US)

(73) Assignee: Philip Morris Products S.A., Neuchatel (CH)

( * ) Notice: Subject to any disclaimer, the term of this patent is extended or adjusted under 35 U.S.C. 154(b) by 321 days.

(21) Appl. No.: 12/054,883

(22) Filed: Mar. 25, 2008

(65) Prior Publication Data

US 2008/0241255 A1 Oct. 2, 2008

Related U.S. Application Data

(60) Provisional application No. 60/909,302, filed on Mar. 30, 2007.

(51) Int. Cl.
*A61K 31/465* (2006.01)
*A61K 31/4439* (2006.01)
*A61M 15/06* (2006.01)
*A61M 11/04* (2006.01)
*A24F 47/00* (2020.01)
*A24B 15/167* (2020.01)
*A24B 15/16* (2020.01)
*A61K 9/00* (2006.01)
*A61K 9/16* (2006.01)
*A61M 15/00* (2006.01)

(52) U.S. Cl.
CPC ............ *A61K 31/465* (2013.01); *A24B 15/16* (2013.01); *A24B 15/167* (2016.11); *A24F 47/002* (2013.01); *A24F 47/004* (2013.01); *A61K 9/007* (2013.01); *A61K 9/1617* (2013.01); *A61K 31/4439* (2013.01); *A61M 11/041* (2013.01); *A61M 15/009* (2013.01); *A61M 15/06* (2013.01); *A61M 11/047* (2014.02); *A61M 15/0091* (2013.01); *A61M 2205/071* (2013.01); *A61M 2205/8206* (2013.01)

(58) Field of Classification Search
CPC . A61K 31/4439; A61M 11/041; A61M 15/06; A61M 11/047; A61M 2205/071; A61M 2205/8206; A61M 15/0091; A24F 47/004
See application file for complete search history.

(56) References Cited

U.S. PATENT DOCUMENTS

| 830,626 | A | | 9/1906 | Van Nes |
| 3,258,015 | A | | 6/1966 | Ellis et al. |
| 3,356,094 | A | | 12/1967 | Ellis et al. |
| 4,148,881 | A | * | 4/1979 | Ishiguro ........................ 424/120 |
| 4,715,387 | A | | 12/1987 | Rose |
| 4,736,755 | A | | 4/1988 | Oldman |
| 4,765,348 | A | | 8/1988 | Honeycutt |
| 4,800,903 | A | | 1/1989 | Ray |
| 4,830,028 | A | | 5/1989 | Lawson et al. |
| 4,836,224 | A | | 6/1989 | Lawson et al. |
| 4,907,605 | A | | 3/1990 | Ray |
| 4,924,886 | A | | 5/1990 | Litzinger |
| 4,955,397 | A | | 9/1990 | Johnson et al. |
| 5,027,836 | A | * | 7/1991 | Shannon et al. ............... 131/194 |
| 5,033,483 | A | | 7/1991 | Clearman et al. |
| 5,050,621 | A | * | 9/1991 | Creighton et al. ............. 131/331 |
| 5,101,838 | A | * | 4/1992 | Schwartz et al. ............. 131/273 |
| 5,105,834 | A | * | 4/1992 | Saintsing et al. ............. 131/334 |
| 5,133,368 | A | | 7/1992 | Neumann |
| 5,316,759 | A | * | 5/1994 | Rose et al. ..................... 514/343 |
| 5,327,915 | A | | 7/1994 | Porenski et al. |
| 5,441,060 | A | * | 8/1995 | Rose et al. ..................... 131/271 |
| 5,538,020 | A | | 7/1996 | Farrier et al. |
| 6,102,036 | A | * | 8/2000 | Slutsky et al. ............ 128/203.15 |
| 6,772,756 | B2 | | 8/2004 | Shayan |
| 6,929,004 | B1 | | 8/2005 | Bonney et al. |
| 6,990,978 | B2 | | 1/2006 | Shayan |
| 7,168,431 | B2 | | 1/2007 | Li et al. |
| 2002/0017295 | A1 | | 2/2002 | Weers et al. |
| 2004/0009128 | A1 | | 1/2004 | Rabinowitz et al. |
| 2004/0034068 | A1 | | 2/2004 | Warchol et al. |
| 2005/0053665 | A1 | | 3/2005 | Ek et al. |
| 2005/0107772 | A1 | | 5/2005 | Chen |
| 2005/0267120 | A1 | | 12/2005 | Stenkamp et al. |
| 2006/0018840 | A1 | | 1/2006 | Lechuga-Ballesteros et al. |

(Continued)

FOREIGN PATENT DOCUMENTS

CN 86103434 11/1986
CN 1158734 9/1997

(Continued)

OTHER PUBLICATIONS

Bates, Tobacco Additives, 1999.*
Hughes, T.W., et al., Nicotine Administration Ariel Smoking Devices, Produced during Minnesota Tobacco Litigation Case No. C1-94-8565, document dated Jul. 28, 1966.
Battelle Memorial Institute, Research Proposal regarding Project Ariel, Produced during Tobacco Litigation Case No. C1-94-8565, document dated Jan. 3, 1962.
Glantz, Stanton A., et al., Chapter 3 Addiction and Cigarettes as Nicotine Delivery Devices, the Cigarette Papers, 1996, 74-77, University of California Press, Berkeley, USA, available in full at: http://publishing.cdlib.org/ucpressebooks/view?docId=ft8489p25j;brand=eschol.

(Continued)

Primary Examiner — Susan T Tran
Assistant Examiner — William Craigo
(74) Attorney, Agent, or Firm — Mueting Raasch Group

(57) ABSTRACT

The disclosure relates to a method of enhancing nicotine or other medicament concentrations in a gaseous carrier. The methods are adaptable to the delivery of nicotine or other medicaments for therapeutic effect in various diseases, in particular nicotine for tobacco product use cessation, substitution and/or harm reduction. The disclosure further relates various devices and device design principles for practicing these methods.

24 Claims, 13 Drawing Sheets

(56) References Cited

U.S. PATENT DOCUMENTS

| | | | |
|---|---|---|---|
| 2006/0027243 A1 | 2/2006 | Matsufuji et al. | |
| 2007/0062548 A1* | 3/2007 | Horstmann et al. | 131/270 |
| 2008/0241255 A1 | 10/2008 | Rose et al. | |
| 2013/0276804 A1 | 10/2013 | Hon | |

FOREIGN PATENT DOCUMENTS

| | | |
|---|---|---|
| CN | 1889861 | 1/2007 |
| EP | 0003064 | 7/1979 |
| EP | 0148749 A2 | 7/1985 |
| EP | 0354661 | 2/1990 |
| EP | 0354661 A2 | 2/1990 |
| EP | 0471581 | 2/1992 |
| EP | 0520231 | 12/1992 |
| EP | 0364805 | 2/1994 |
| EP | 0337508 | 8/1995 |
| EP | 0712584 A1 | 5/1996 |
| EP | 1477119 | 11/2004 |
| GB | 248751 B1 | 1/1927 |
| GB | 2199229 A | 7/1988 |
| GB | 2199229 | 7/1990 |
| JP | 63152968 A | 6/1988 |
| JP | H01104153 A | 4/1989 |
| JP | 0217117 A | 7/1990 |
| JP | H02190178 A | 7/1990 |
| JP | 03090163 A | 4/1991 |
| JP | 04229166 A | 8/1992 |
| JP | 2001161819 A | 6/2001 |
| JP | 2005522206 A | 7/2005 |
| JP | 2007512880 A | 5/2007 |
| KR | 19980008081 | 4/1998 |
| KR | 2000-0021999 | 4/2000 |
| RU | 2336001 C2 | 10/2008 |
| WO | 2004091325 A1 | 10/2004 |
| WO | WO 2005053444 A1 * | 6/2005 |
| WO | 2006/070288 A2 | 7/2006 |
| WO | 2007/042941 A2 | 4/2007 |
| WO | 2008121610 A1 | 10/2008 |

OTHER PUBLICATIONS

Reuter, B., [Title Unknown], The Legacy Tobacco Documents Library, May 24, 1999, pp. 1-12, University of California, San Francisco, available at http://legacy.library.ucst.edu/tid/mzf12a00.

Response to First Written Opinion dated Sep. 19, 2008, during the prosecution of International application No. PCT/US2008/58122.

International Search Report dated Jul. 9, 2008, during the prosecution of International application PCT/2008/058122, Published Oct. 9, 2008.

Written Opinion dated Jul. 9, 2008, during the prosecution of International application PCT/2008/058122, Published Oct. 9, 2008.

Crouse, William E. et al., "Nicotine Extraction Preliminary Study of Methods for High Nicotine Leaf Extraction", Lorillard Research Center Greensboro, Jun. 29, 1976.

Japanese Examination Report dated Sep. 5, 2014 issued in related JP Application No. 2012-500827, with English translation.

Office Action issued in Europe for Application No. 08744313.1 dated May 28, 2015 (7 pages).

Office Action issued in Australian for Application No. 2014200827 dated Apr. 13, 2015 (6 pages).

Office Action issued in China for Application No. 201510173107.0 dated Jun. 28, 2017 (18 pages). English translation included.

Office Action issued in Europe for Application No. 08744313.1-1664 dated May 2, 2017 (5 pages).

Office Action issued in India for Application No. 2525/DELNP/2014 dated Oct. 10, 2019 (6 pages). English translation included.

Office Action issued in China for Application No. 201510173107.0 dated Nov. 1, 2019 (16 pages). English translation included.

High-Tech Fiber, Chemistry Industry Press, pp. 85-88 dated Sep. 30, 2004.

* cited by examiner

DEVICE AND METHOD FOR DELIVERY OF A MEDICAMENT

TECHNICAL FIELD

The invention relates to devices and methods for delivering a medicament to a user. More particularly, the invention relates to devices and methods for delivering an aerosol of a medicament to a user's lungs.

BACKGROUND ART

Pulmonary drug delivery systems have been used for decades to deliver medicaments for the treatment of respiratory disorders. The principle behind pulmonary drug delivery is aerosolization of drug compounds to be delivered to bronchioles and alveoli. Despite facing challenges like particle size optimization and degradation, a number of companies have developed technologies to deliver treatments for diabetes, migraine, osteoporosis and cancer.

The available delivery systems include metered dose inhalers (MDIs), dry powder inhalers (DPIs), and nebulizers. MDIs were among the first to be introduced in the United States in the mid 1950s. The HFA-based (pressurized) MDI was introduced in the United States in 1995. Although DPIs were introduced in the 1970s, their use has been limited due to the overwhelming dominance of MDIs. Nebulizers are generally used within hospital settings. Technological advances within the pulmonary drug delivery technologies markets are taking place in non-CFC-based MDIs, DPIs, and liquid-based inhalers (LBIs).

Many preclinical and clinical studies have demonstrated that pulmonary delivery of medicaments is an efficient method for the treatment of both respiratory and systemic diseases. The many advantages of pulmonary delivery are well recognized and include rapid onset, patient self-administration, reduced side-effects, ease of delivery by inhalation, and the elimination of needles.

Nevertheless, methods for the administration of most medicaments have not significantly deviated from delivery via the traditional intravenous/intramuscular and oral routes to include pulmonary delivery via inhalation. The use of pulmonary delivery has been limited mainly to the administration of medicaments for the treatment of asthma.

It has been reported that in order to deliver a powder directly into the lower respiratory regions the powder should generally have a particle size of less than 5 µm. Further, powders in the 5-10 µm range have been found not to penetrate as deeply and instead tend to stimulate the upper respiratory tract regions.

When manufacturing drug formulations for dry powder inhalers (DPIs), the medicament must first be milled to obtain an acceptable particle size for pulmonary delivery. This micronization step can cause problems during manufacture. For example, the heat produced during milling can cause degradation of the medicament. Additionally, metal can rub off some mills and contaminate the medicament. Furthermore, due to the small size of the particles, dry powder formulations tend to agglomerate, especially in the presence of moisture.

Agglomeration results in low flowability of the particles which diminishes the efficacy of the dry powder formulation. As a result, careful supervision is required during milling, blending, powder flow, filling and even administration to ensure that the dry powder aerosols are properly delivered.

Thus, there is a need for new methods to prepare aerosols for medicament delivery. The present disclosure describes in part a method for combining nicotine or other medicaments with a delivery enhancing compound in a gaseous stream to generate an aerosol for pulmonary delivery, without the need for excipients or other additives including solvents.

DISCLOSURE OF INVENTION

Brief Summary of the Invention

In some embodiments, the disclosure relates to a method of delivering nicotine to a subject by inhalation, the method comprising the steps of:
   a) first placing a gaseous carrier comprising a delivery enhancing compound in communication with a nicotine source comprising the nicotine, and
   b) second providing the gaseous carrier comprising the nicotine to a subject.

In some embodiments, the disclosure relates to the method of paragraph [0010], further comprising the step of placing the gaseous carrier in communication with a delivery enhancing compound source comprising the delivery enhancing compound.

In some embodiments, the disclosure relates to the method of [0011], wherein the step of placing the gaseous carrier in communication with the delivery enhancing compound source precedes the step of placing the gaseous carrier comprising the delivery enhancing compound in communication with the nicotine source.

In some embodiments, the disclosure relates to the method of [0010], [0011], or [0012], wherein the delivery enhancing compound source comprises a plurality of compartments comprising two or more precursor compounds.

In some embodiments, the disclosure relates to the method of [0013], wherein the delivery enhancing compound comprises ammonium chloride and the two or more precursor compounds include ammonia and hydrogen chloride.

In some embodiments, the disclosure relates to the methods of [0010]-[0013], or [0014], wherein the nicotine concentration in the gaseous carrier is increased relative to the nicotine concentration that would be contained in the gaseous carrier without the delivery enhancing compound.

In some embodiments, the disclosure relates to the methods of [0010]-[0014], or [0015], wherein the delivery enhancing compound comprises an acid.

In some embodiments, the disclosure relates to the method of [0016], wherein the acid is an organic acid.

In some embodiments, the disclosure relates to the method of [0017], wherein the organic acid has a greater vapor pressure than nicotine base at a given temperature.

In some embodiments, the disclosure relates to the method of [0018], wherein the given temperature is 25, 30, 40, 45, 70 or 100 degrees C.

In some embodiments, the disclosure relates to the methods of [0016]-[0018], or [0019] wherein the acid is selected from the group consisting of 3-Methyl-2-oxovaleric acid, Pyruvic acid, 2-Oxovaleric acid, 4-Methyl-2-oxovaleric acid, 3-Methyl-2-oxobutanoic acid, 2-Oxooctanoic acid and combinations thereof.

In some embodiments, the disclosure relates to the methods of [0010]-[0019], or [0020], wherein the delivery enhancing compound interacts with the nicotine to form particles.

In some embodiments, the disclosure relates to the method of [0021], wherein the particles are less than 6 microns in Mass Median Aerodynamic Diameter.

In some embodiments, the disclosure relates to the method of [0021], wherein the particles are less than 1 micron in Mass Median Aerodynamic Diameter.

In some embodiments, the disclosure relates to the method of [0021], wherein at least some of the particles are between 0.5 and 5 microns in Mass Median Aerodynamic Diameter.

In some embodiments, the disclosure relates to the methods of [0010]-[0023], or [0024], further comprising the step of increasing the temperature of the delivery enhancing compound, the delivery enhancing compound source, the nicotine, the nicotine source and/or the gaseous carrier.

In some embodiments, the disclosure relates to the method of [0025], wherein the temperature is increased to at least 30 degrees Celsius.

In some embodiments, the disclosure relates to the methods of [0010]-[0025], or [0026], wherein the gaseous carrier comprises at least 20 micrograms of nicotine in a volume of gaseous carrier provided to the subject.

In some embodiments, the disclosure relates to the method of [0027], wherein the volume of gaseous carrier delivered to the subject is provided as a single volume.

In some embodiments, the disclosure relates to a method of tobacco product use cessation comprising one or more of the methods of [0010]-[0027], or [0028] and further comprising a delivery to the subject of a therapeutically effective amount of nicotine to at least partially replace nicotine derived from a tobacco product.

In some embodiments, the disclosure relates to a method of treating a disease for which nicotine is therapeutically beneficial comprising one or more of the methods of [0010]-[0027], or [0028], wherein a therapeutically effective amount of nicotine is provided to the subject.

In some embodiments, the disclosure relates to the method of [0030], wherein the disease is selected from the group consisting of nicotine addiction, obesity, Alzheimer's Disease, Parkinson's Disease, Ulcerative Colitis, Multiple Sclerosis and combinations thereof.

In some embodiments, the disclosure relates to a method of tobacco product substitution comprising delivering nicotine to a subject by the methods of [0010]-[0027], or [0028] to substitute for nicotine derived from a tobacco product.

In some embodiments, the disclosure relates to a method of tobacco product harm reduction comprising delivering nicotine to a subject by the methods of [0010]-[0027], or [0028] to replace nicotine derived from a tobacco product.

In some embodiments, the disclosure relates to a device configured to be capable of carrying out the methods of [0010]-[0032], or [0033].

In some embodiments, the disclosure relates to a device for delivering nicotine to a subject, the device comprising a housing, the housing comprising:

a) an inlet and an outlet in communication with each other and adapted so that a gaseous carrier may pass into the housing through the inlet, through the housing and out of the housing through the outlet, the device comprising in series from inlet to outlet:
b) a first internal area in communication with the inlet, the first internal area comprising a delivery enhancing compound source,
c) a second internal area in communication with the first internal area, the second internal area comprising a nicotine source, and
d) optionally, a third internal area in communication with the second internal area and the outlet.

In some embodiments, the disclosure relates to the device of [0035] wherein a partial vacuum at the outlet is capable of pulling the gaseous carrier through the inlet, the first compartment, the second compartment, the third compartment, when present, and then through the outlet.

In some embodiments, the disclosure relates to the device of [0035] or [0036] wherein the delivery enhancing compound source comprises an adsorption element with the delivery enhancing compound adsorbed thereon and/or wherein the nicotine source comprises an adsorption element with the nicotine adsorbed thereon.

In some embodiments, the disclosure relates to the device of [0037] wherein the adsorption element or elements comprises at least one of glass, aluminum, Polyethylene Terephthalate (PET), Polybutylene Terephthalate (PBT), Polytetrafluoroethylene (PTFE or TEFLON®), Expanded Polytetrafluoroethylene (ePTFE) (ePTFE is described for example in U.S. Pat. No. 4,830,643), and BAREX®.

In some embodiments, the disclosure relates to the devices of [0035]-[0037], or [0038], further comprising a first reservoir in communication with the first internal area, the first reservoir comprising the delivery enhancing compound.

In some embodiments, the disclosure relates to the devices of [0035]-[0038], or [0039], further comprising a second reservoir in communication with the second internal area, the second reservoir comprising nicotine.

In some embodiments, the disclosure relates to the devices of [0035]-[0039], or [0040], comprising the third internal area, the third internal area comprising a third internal area element.

In some embodiments, the disclosure relates to the device of [0041], wherein the third internal area element comprises a purifying agent.

In some embodiments, the disclosure relates to the device of [0042], wherein the purifying agent comprises activated charcoal.

In some embodiments, the disclosure relates to the devices of [0041], [0042], or [0043], wherein the third internal area element comprises a flavoring agent.

In some embodiments, the disclosure relates to the devices of [0041]-[0043], or [0044], where the third internal area element comprises a medicament.

In some embodiments, the disclosure relates to the device of [0045], wherein the medicament comprises nicotine.

In some embodiments, the disclosure relates to the devices of [0035]-[0045], or [0046], wherein the housing simulates a tobacco smoking product.

In some embodiments, the disclosure relates to the device of [0047], wherein the tobacco smoking product is a cigarette.

In some embodiments, the disclosure relates to the devices of [0035]-[0045], or [0046], wherein the housing simulates a pharmaceutical inhalation device.

In some embodiments, the disclosure relates to the device of [0049], wherein the simulated pharmaceutical inhalation device is selected form the group consisting of a metered dose inhaler, a pressurized metered dose inhaler, a dry powder inhaler, a nebulizer, and a liquid based inhaler.

In some embodiments, the disclosure relates to a method of increasing a nicotine concentration in a gaseous carrier comprising a step of placing the gaseous carrier comprising a delivery enhancing compound in communication with a nicotine source comprising the nicotine.

In some embodiments, the disclosure relates to the method of [0051], further comprising the step of placing the gaseous carrier in communication with a delivery enhancing compound source comprising the delivery enhancing compound.

In some embodiments, the disclosure relates to the method of [0052], wherein the step of placing the gaseous carrier in communication with the delivery enhancing compound source precedes the step of placing the gaseous carrier comprising the delivery enhancing compound in communication with the nicotine source.

In some embodiments, the disclosure relates to the method of [0051], [0052], or [0053], wherein the delivery enhancing compound source comprises a plurality of compartments comprising two or more precursor compounds.

In some embodiments, the disclosure relates to the method of [0054], wherein the delivery enhancing compound comprises ammonium chloride and the two or more precursor compounds include ammonia and hydrogen chloride.

In some embodiments, the disclosure relates to the method of [0051]-[0054], or [0055], wherein the nicotine concentration in the gaseous carrier is increased relative to the nicotine concentration that would be contained in the gaseous carrier without the delivery enhancing compound.

In some embodiments, the disclosure relates to the method of [0051]-[0055], or [0056], wherein the delivery enhancing compound comprises an acid.

In some embodiments, the disclosure relates to the method of [0057], wherein the acid is an organic acid.

In some embodiments, the disclosure relates to the method of [0058], wherein the organic acid has a greater vapor pressure than nicotine at a given temperature.

In some embodiments, the disclosure relates to the method of [0059], wherein the given temperature is 25, 30, 40, 45, 70 or 100 degrees Celsius.

In some embodiments, the disclosure relates to the method of [0057], wherein the acid is selected from the group consisting of 3-Methyl-2-oxovaleric acid, Pyruvic acid, 2-Oxovaleric acid, 4-Methyl-2-oxovaleric acid, 3-Methyl-2-oxobutanoic acid, 2-Oxooctanoic acid and combinations thereof.

In some embodiments, the disclosure relates to the method of [0051]-[0060], or [0061], wherein the delivery enhancing compound interacts with the nicotine to form particles.

In some embodiments, the disclosure relates to the method of [0062], wherein some or all of the particles are less than 6 microns in Mass Median Aerodynamic Diameter.

In some embodiments, the disclosure relates to the method of [0062], wherein some or all of the particles are less than 1 micron in Mass Median Aerodynamic Diameter.

In some embodiments, the disclosure relates to the method of [0062], wherein at least some of the particles are between 0.5 and 5 microns in Mass Median Aerodynamic Diameter.

In some embodiments, the disclosure relates to the method of [0051]-[0064], or [0065], further comprising the step of increasing the temperature of the delivery enhancing compound, the delivery enhancing compound source, the nicotine, the nicotine source and/or the gaseous carrier.

In some embodiments, the disclosure relates to the method of [0066], wherein the temperature is increased to at least 30 degrees Celsius.

In some embodiments, the disclosure relates to the method of [0067], wherein the temperature is elevated by a plurality of heating steps.

In some embodiments, the disclosure relates to a nicotine for tobacco product use cessation, the nicotine delivered by the method of [0051]-[0067], or [0068], further comprising the step of providing the gaseous carrier to a subject after the step of placing the gaseous carrier comprising the delivery enhancing compound in communication with the nicotine source.

In some embodiments, the disclosure relates to the nicotine of [0069], wherein the gaseous carrier comprises at least 20 micrograms of nicotine in a volume of gaseous carrier provided to the subject.

In some embodiments, the disclosure relates to the nicotine of [0070], wherein the volume of gaseous carrier delivered to the subject is provided as a single volume.

In some embodiments, the disclosure relates to a nicotine for tobacco product harm reduction, the nicotine delivered by the method of [0051]-[0067], or [0068], further comprising the step of providing the gaseous carrier to a subject after the step of placing the gaseous carrier comprising the delivery enhancing compound in communication with the nicotine source.

In some embodiments, the disclosure relates to the nicotine of [0072], wherein the gaseous carrier comprises at least 20 micrograms of nicotine in a volume of gaseous carrier provided to the subject.

In some embodiments, the disclosure relates to the nicotine of [0073], wherein the volume of gaseous carrier delivered to the subject is provided as a single volume.

In some embodiments, the disclosure relates to a nicotine for tobacco product substitution, the nicotine delivered by the method of [0051]-[0067], or [0068], further comprising the step of providing the gaseous carrier to a subject after the step of placing the gaseous carrier comprising the delivery enhancing compound in communication with the nicotine source.

In some embodiments, the disclosure relates to the nicotine of [0075], wherein the gaseous carrier comprises at least 20 micrograms of nicotine in a volume of gaseous carrier provided to the subject.

In some embodiments, the disclosure relates to the nicotine of [0076], wherein the volume of gaseous carrier delivered to the subject is provided as a single volume.

In some embodiments, the disclosure relates to a nicotine for the treatment of a disease selected from the group consisting of nicotine addiction, obesity, Alzheimer's Disease, Parkinson's Disease, Ulcerative Colitis, Multiple Sclerosis and combinations thereof, the nicotine delivered by the method of [0051]-[0067], or [0068], further comprising the step of providing the gaseous carrier to a subject after the step of placing the gaseous carrier comprising the delivery enhancing compound in communication with the nicotine source.

In some embodiments, the disclosure relates to a device configured to be capable of carrying out a) the method of [0051]-[0067], or [0068]; and/or b) configured to be capable of delivering the nicotine of [0069]-[0077], or [0078].

In some embodiments, the disclosure relates to a use of nicotine for the manufacture of a medicament for delivery by the method of [0051]-[0067], or [0068].

In some embodiments, the disclosure relates to a use of nicotine for the manufacture of a medicament for tobacco product use cessation for delivery by the method of [0051]-[0067], or [0068].

In some embodiments, the disclosure relates to a use of nicotine for the manufacture of a medicament for tobacco product harm reduction for delivery by the method of [0051]-[0067], or [0068].

In some embodiments, the disclosure relates to a use of nicotine for the manufacture of a medicament for tobacco product substitution for delivery by the method of [0051]-[0067], or [0068].

In some embodiments, the disclosure relates to a use of nicotine for the manufacture of a medicament for the treatment of a disease selected from the group consisting of nicotine addiction, obesity, Alzheimer's Disease, Parkinson's Disease, Ulcerative Colitis, Multiple Sclerosis and combinations thereof, the nicotine delivered by the method of [0051]-[0067], or [0068], further comprising the step of providing the gaseous carrier to a subject after the step of placing the gaseous carrier comprising the delivery enhancing compound in communication with the nicotine source.

In some embodiments, the disclosure relates to a method for delivering a medicament to a user, the method comprising:

passing a gaseous stream over a first substance to create a first vapor-containing gaseous stream;

passing the first vapor-containing gaseous stream over a second substance to create particles in the gaseous stream; and delivering the gaseous stream containing the particles to a user.

In some embodiments, the disclosure relates to the method of [0085], wherein the step of creating the first vapor-containing gaseous stream comprises capturing a vapor of the first substance in the gaseous stream.

In some embodiments, the disclosure relates to the method of [0085] or [0086], wherein the step of creating particles comprises contacting a vapor of the second substance with the first vapor-containing gaseous stream.

In some embodiments, the disclosure relates to the method of [0085], [0086], or [0087], wherein the step of creating the particles comprises an interaction between the first and second substances.

In some embodiments, the disclosure relates to the method of [0088], where said interaction comprises an acid-base reaction.

In some embodiments, the disclosure relates to the method of [0085]-[0088], or [0089], where the first and second substances are volatile substances.

In some embodiments, the disclosure relates to the method of [0090], wherein the first substance is more volatile at ambient temperature than the second substance.

In some embodiments, the disclosure relates to the method of [0085]-[0090], or [0091], wherein one of the first substance and/or the second substance comprises a nicotine.

In some embodiments, the disclosure relates to the method of [0092], wherein the nicotine comprises free base nicotine.

In some embodiments, the disclosure relates to the method of [0085]-[0092], or [0093], wherein the particles comprise nicotine-containing particles.

In some embodiments, the disclosure relates to the method of [0085]-[0093], or [0094], wherein the gaseous stream delivered to a user contains more than 20 micrograms of nicotine-containing particles.

In some embodiments, the disclosure relates to the method of [0085]-[0094], or [0095], wherein the particles comprise nicotine salt particles.

In some embodiments, the disclosure relates to the method of [0085]-[0095], or [0096], wherein the first substance comprises an acid.

In some embodiments, the disclosure relates to the method of [0097], wherein the acid comprises pyruvic acid.

In some embodiments, the disclosure relates to the method of [0085]-[0097], or [0098], wherein the particles comprise nicotine pyruvate.

In some embodiments, the disclosure relates to the method of [0097], wherein the acid comprises 3-methyl-2-oxobutanoic acid.

In some embodiments, the disclosure relates to the method of [0085]-[0099], or [0100], wherein the particles comprise nicotine 3-methyl-2-oxobutanoate.

In some embodiments, the disclosure relates to the method of [0085]-[0100], or [0101], wherein at least some of the particles are visible particles.

In some embodiments, the disclosure relates to the method of [0085]-[0101], or [0102], wherein at least some of the particles are delivered to the lungs of the user.

In some embodiments, the disclosure relates to the method of [0085]-[0102], or [0103], wherein the particles are less than 6 microns in diameter.

In some embodiments, the disclosure relates to the method of [0085]-[0103], or [0104], wherein at least some of the particles are between 0.5 and 5 microns in diameter.

In some embodiments, the disclosure relates to the method of [0010]-[0027], or [0028]; or the method of [0051]-[0067], or [0068]; or the use of [0080] wherein a medicament listed at [0132], such as a compound identified by numbers 1-66 in [0132], is used instead, of or in addition to, the nicotine recited in [0010]-[0027], or [0028]; [0051]-[0067], or [0068]; or [0080].

In some embodiments, the disclosure relates to the device of [0035]-[0049], or [0050] wherein the device is adapted to deliver a medicament listed in [0132], such as a compound identified by numbers 1-66 in [0132], instead of, or in addition to, the nicotine.

In some embodiments, the disclosure relates to use of a medicament of [0132], such as a compound identified by numbers 1-66 in [0132], for delivery by the methods of [0010]-[0027], or [0028]; or [0051]-[0067], or [0068] for treatment of a disease for which the medicament is therapeutically beneficial.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF DRAWINGS

For a more complete understanding of the present invention, reference is now made to the following descriptions taken in conjunction with the accompanying drawing, in which.

DETAILED DESCRIPTION

Figure 1:
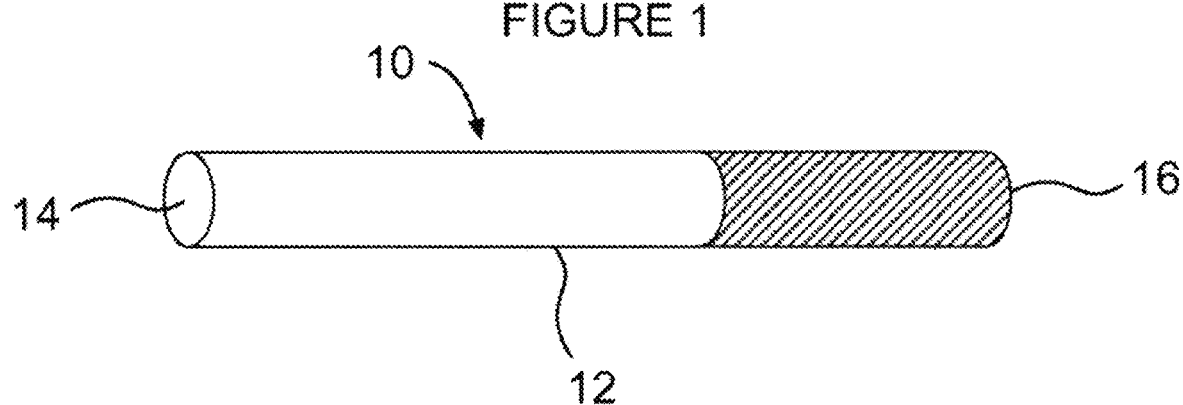
FIG. 1 a perspective view of the exterior of an exemplary delivery device simulating a cigarette.

"Particle" as used herein may refer to a liquid droplet, a solid particulate or a combination of both, such as a liquid droplet nucleated by a solid particulate.

"Therapeutically effective amount" as used herein may refer to a concentration or amount of nicotine or other medicament which achieves a therapeutic effect in a subject, generally a human subject. The subject has an improvement in a disease or medically defined condition. The improvement is any improvement or remediation of the symptoms associated with the disease. The improvement is an observable or measurable improvement. Thus, one of skill in the art realizes that a treatment may improve the disease condition, but may not be a complete cure for the disease. The therapeutic effect in some embodiments may include reduction or elimination of nicotine craving in a subject suffering nicotine addiction or in a subject experiencing nicotine use withdrawal symptoms.

To aid in the understanding of the concepts of the present invention, embodiments will be described herein with reference to devices and methods for nicotine delivery. It will be appreciated by one of ordinary skill in the art that the medicaments listed at [0132] may be used in place of or in addition to the nicotine according to the teachings herein.

The methods described herein relate to a surprising discovery regarding the dose of nicotine obtained from nicotine delivery devices. The inventors have unexpectedly identified methods for increasing the dose of nicotine delivered to a subject by inhalation. The importance of this discovery lies in an improved ability to substitute for the nicotine delivery subjects experience while smoking cigarettes and similar tobacco products. With improved nicotine delivery profiles, subjects applying the methods described herein will be provided with superior nicotine replacement therapy during attempts at smoking cessation, harm reduction and/or substitution. With the continued global problem of smoking related health issues, the methods described herein address a critical need in medical efforts to assist smokers in quitting.

Without desiring to be bound by theory, it is believed that passing the vapor of a volatile first substance (i.e. a delivery enhancing compound) over a nicotine source results in the formation of particles in a liquid or solid state, which subsequently allows more of the nicotine to evaporate and combine with the first substance, generating further particles. The amount of particle formation (mass delivered) at a given temperature would be greater than that formed when the vapor of nicotine is passed over a second volatile substance. Similarly, the amount of particle formation at a given temperature would be greater than that formed when the vapors of the two substances are combined in a parallel mixing apparatus (as disclosed in prior art), due to the amount of particle formation being limited by the volatility of the less volatile substance and to the dilution of the active substance by mixing with the volume of gas containing the other substance. Also, allowing sequential passing of one substance over a second substance may allow for a more efficient combination of the two substances than parallel mixing as disclosed in prior art. Another possibility is that the interaction between the first and second substances is an exothermic process. In other words, energy is released in the form of heat as a result of the exothermic interaction. Without desiring to be bound by theory, it is believed that the heat released may enhance the evaporation of the nicotine.

In some embodiments, the methods involve the step of bringing a gaseous carrier in communication with a nicotine source. The gaseous carrier in these embodiments contains a delivery enhancing compound capable of increasing the amount of nicotine in the gaseous carrier, relative to the amount of nicotine that would be in the gaseous carrier lacking the delivery enhancing compound. In some embodiments, the delivery enhancing compound is capable of reacting with nicotine base or other medicament to form a salt. In particular embodiments, the delivery enhancing compound is capable of reacting with nicotine base to form salt particles. In preferred embodiments, the particles are less than 6 micrometers, more preferably less than 1 micrometer, in Mass Median Aerodynamic Diameter. (For Mass Median Aerodynamic Diameter determinations, see Katz I M, Schroeter J D, Martonen T B, Factors affecting the deposition of aerosolized insulin, *Diabetes technology & Therapeutics*, vol. 3 (3), 2001, pp 387-397, incorporated by reference for this teaching).

The methods disclosed herein may be adapted for use with a variety of other medicaments having similar biophysical and/or chemical properties to nicotine. The following compounds are aliphatic or aromatic, saturated or unsaturated nitrogenous bases (nitrogen containing alkaline compounds) in which a nitrogen atom is present in a heterocyclic ring or in an acyclic chain (substitution). In addition, the compounds have been selected based on melting point (below 150° C.) or boiling point (below 300° C.) that are expected to favor volatilization:

| Medicaments - other than Nicotine |
|---|
| 1. 7-Hydroxymitragynine |
| 2. Arecoline |
| 3. Atropine |
| 4. Bupropion |
| 5. Cathine (D-norpseudoephedrine) |
| 6. Chlorpheneramine |
| 7. Dibucaine |
| 8. Dimemorphan |
| 9. Dimethyltryptamine |
| 10. Diphenhydramine |
| 11. Ephedrine |
| 12. Hordenine |
| 13. Hyoscyamine |
| 14. Isoarecoline |
| 15. Levorphanol |
| 16. Lobeline |
| 17. Mesembrine |
| 18. Mitragynine |
| 19. Muscarine |
| 20. Procaine |
| 21. Pseudo ephedrine |
| 22. Pyrilamine |
| 23. Raclopride |
| 24. Ritodrine |
| 25. Scopolamine |
| 26. Sparteine (Lupinidine) |
| 27. Ticlopidine |
| Tobacco Smoke Constituents: |
| 28. 1,2,3,4-Tetrahydroisoquinolines |
| 29. Anabasine |
| 30. Anatabine |
| 31. Cotinine |
| 32. Myosmine |
| 33. Nicotrine |
| 34. Norcotinine |
| 35. Nornicotine |
| Anti-asthmatic drugs |
| 36. Orciprenaline |
| 37. Propranolol |
| 38. Terbutaline |
| Anti-angina drugs |
| 39. Nicorandil |
| 40. Oxprenolol |
| 41. Verapamil |
| Antiarrhythmic drugs |
| 42. Lidocaine |
| Nicotinic receptor agents |
| A. Nicotinic agonist |
| 43. Epibatidine |
| 44. 5-(2R)-azetidinylmethoxy)-2-chloropyridine (ABT-594) |
| 45. (S)-3-methyl-5-(1-methyl-2-pyrrolidinyl)isoxazole (ABT 418) |

-continued

| |
|---|
| 46. (±)-2-(3-Pyridinyl)-1-azabicyclo[2.2.2]octane (RJR-2429) |
| B. Nicotinic antagonist: |
| 47. Methyllycacotinine |
| 48. Mecamylamine |
| C. Acetyl cholinesterase inhibitors |
| 49. Galantamine |
| 50. Pyridostigmine |
| 51. Physostigmine |
| 52. Tacrine |
| MAO-inhibitors |
| 53. 5-Methoxy-N,N-dimethyltryptamine |
| 54. 5-methoxy-α-methyltryptamine |
| 55. Alpha-methyltryptamine |
| 56. Iproclozide |
| 57. Iproniazide |
| 58. Isocarboxazide |
| 59. Linezolid |
| 60. Meclobemide |
| 61. N,N-Dimethyltryptamine |
| 62. Phenelzine |
| 63. Phenyl ethylamine |
| 64. Toloxatone |
| 65. Tranylcypromine |
| 66. Tryptamine |

Gaseous Carrier and Source Thereof

The gaseous carrier may be any gas capable of containing nicotine base and the delivery enhancing compound. One of skill in the art will readily be able to select an appropriate gaseous carrier based on the intended use, form of nicotine and specific delivery enhancing compound(s). In preferred embodiments, the gaseous carrier is substantially inert with regard to the form of nicotine and/or the delivery enhancing compound carried, at least for the time period contemplated for delivery to a subject. In some embodiments, the gaseous carrier is ambient air. In other embodiments the gaseous carrier is a substantially pure gas such as carbon dioxide or nitrogen gas, or a blend of such gases. In such embodiments, the gaseous carrier is supplied from a container designed to hold and deliver the gaseous carrier in a manner to effect the methods described herein. For example, in embodiments using metered dose inhaler devices, the gaseous carrier may comprise Hydrofluorocarbons, which include Hydrofluoroalkanes (HFAs) as propellants. In some of these embodiments, the HFAs, are one or more of HFA 134a and HFA 227.

Delivery Enhancing Compounds

Delivery enhancing compounds are those compounds capable of increasing the total concentration of nicotine in a gaseous carrier when the gaseous carrier is placed in communication with a nicotine source. Nicotine has a vapor pressure of 0.04 mm Hg at 25° C. Delivery enhancing compounds having a vapor pressure greater than nicotine at a given temperature are preferred if ambient temperatures are used. Non-limiting examples include inorganic acids such as hydrochloric, hydrobromic, or sulfuric acid, and organic acids including saturated and unsaturated aliphatic acids, saturated and unsaturated alicyclic acids, aromatic acids (including heterocyclic aromatic), polycarboxylic acids, hydroxy, alkoxy, keto, and oxo acids, thioacids, amino acids, and each of the preceding optionally substituted with one or more heteroatoms, including but not limited to halogens. In some embodiments, the delivery enhancing compound is a carboxylic acid. In some of these embodiments, the carboxylic acid is in the class termed "2-Oxo acids." In some of these embodiments, the carboxylic acid is in the class of α-Keto acids known as "2-Keto acids." In some of these embodiments, the acid is selected from the group consisting of 3-Methyl-2-oxovaleric acid, Pyruvic acid, 2-Oxovaleric acid, 4-Methyl-2-oxovaleric acid, 3-Methyl-2-oxobutanoic acid, 2-Oxooctanoic acid and combinations thereof. In some embodiments, the delivery enhancing compound forms solid particles, for example salt particles. In other embodiments, the delivery enhancing compound forms a liquid droplet aerosol.

Alternatively, the delivery enhancing compound forms a particulate aerosol, the particles of which may, for example, adsorb or absorb nicotine base. In particular embodiments, the particulate aerosol includes ammonium chloride salt particles. In embodiments comprising nicotine particle formation or nicotine adsorption/absorption onto particles the particles formed are preferably less than 6 microns, more preferably less than 5 microns or less than 1 micron in size.

Nicotine (or Other Medicament) Sources

Embodiments of a nicotine source use a compound comprising any chemical capable of providing a volatile form of nicotine such as nicotine base or nicotine salts (e.g. nicotine-HCl, -ditartrate). Although more than one form of nicotine can be used, free base nicotine is preferred. The nicotine source may comprise other compounds such as antioxidants (BHA, BHT, ascorbate) for stabilizing the nicotine. In some embodiments, nicotine is adsorbed on an element to provide a nicotine source. The adsorbed nicotine is held on the surface of a relatively inert material. Non-limiting examples of adsorption element materials include glass, stainless steel, aluminum, PET, PBT, PTFE, ePTFE, and BAREX®. Adsorption is a process that occurs when a gas, liquid or solid solute accumulates on the surface of a solid or, more rarely, a liquid (adsorbent), forming a molecular or atomic film (the adsorbate). Physical adsorption is typically the result of van der Waals forces and electrostatic forces between adsorbate molecules and the atoms which compose the adsorbent surface. Thus adsorbents are characterized by surface properties such as surface area and polarity.

A large specific surface area is preferable for providing large adsorption capacity, but the creation of a large internal surface area in a limited volume inevitably gives rise to large numbers of small sized pores between adsorption surfaces. The size of the micropores determines the accessibility of adsorbate molecules to the internal adsorption surface, so the pore size distribution of micropores is another important property for characterizing adsorptivity of adsorbents. Surface polarity corresponds to affinity with polar substances such as water or alcohols. Polar adsorbents are thus called "hydrophilic" and aluminosilicates such as zeolites, porous alumina, silica gel or silica-alumina are examples of adsorbents of this type. On the other hand, non-polar adsorbents are generally "hydrophobic." Carbonaceous adsorbents, polymer adsorbents and silicalite are typical non-polar adsorbents. These adsorbents have more affinity with oil or hydrocarbons than water. In some embodiments, the adsorbing surface also wicks the adsorbed material by capillary action, when the adsorbent is in liquid form. Wicking occurs when the adhesive intermolecular forces between the liquid and an adsorbing surface are stronger than the cohesive intermolecular forces inside the liquid. The effect causes a concave meniscus to form where the substance is touching a vertical adsorbing surface. Adsorbing surfaces may be selected or designed to wick hydrophilic or hydrophobic liquids.

In alternative embodiments, the nicotine source element can comprise an absorbing (either porous or nonporous) material. Non-limiting examples of nicotine source element materials include polyethylene (PE) and polypropylene (PP).

A nicotine source may in some embodiments be or be in communication with a nicotine reservoir. In some embodiments, the reservoir contains a volume of nicotine in liquid form with the liquid reservoir in communication with an adsorbing or absorbing nicotine source element. In other embodiments, the nicotine reservoir is or forms part of the nicotine source element. A non-limiting example of such a combination source and reservoir would be a material (e.g., PE or PP) saturated with nicotine solution. In particular embodiments, the reservoir provides sufficient nicotine solution to enable a delivery device to provide therapeutically effective doses of nicotine over a desired time frame. Non-limiting examples would be devices capable of delivering 0-100 micrograms of nicotine per 35 cubic centimeter volume "puff" of gaseous carrier for a desired number of puffs per day (e.g., 200) over a desired number of days (e.g., 1-7 days). In certain embodiments, the amount of nicotine delivered is between 10 and 110, 20 and 100, 50 and 100, or 40 and 60 micrograms of nicotine per 35 cubic centimeter volume "puff."

Other medicaments listed in [0132] may be used in place of or in addition to nicotine to form sources of medicament(s) using the same principles applied to nicotine base as the example species above.

Delivery Enhancing Compound Sources

In some embodiments of the methods, the gaseous carrier is provided pre-combined with the delivery enhancing compound. Other embodiments of the methods described herein include a step of loading a gaseous carrier with a delivery enhancing compound prior to or concurrently with passage of the gaseous carrier over the nicotine source. In embodiments encompassing a step of loading gaseous carrier with a delivery enhancing compound, the delivery enhancing compound is generally provided in the form of a delivery enhancing compound source. The gaseous carrier in these embodiments is generally brought into direct communication with the delivery enhancing compound source such that the delivery enhancing compound may enter the gaseous carrier from the delivery enhancing compound source. In some embodiments, delivery enhancing compound sources comprise a delivery enhancing compound source element containing materials which adsorb or absorb the delivery enhancing compound. Delivery enhancing compound source element materials will generally be inert with respect to the delivery enhancing compound. In some embodiments, the delivery enhancing compound is an acid as described above. Non-limiting examples of adsorption element materials for such embodiments include glass, stainless steel, aluminum, PET, PBT, PTFE, ePTFE, and BAREX®. Non-limiting examples of absorption element materials for such embodiments include PE and PP.

A delivery enhancing compound source may in some embodiments be, or be in communication with, a delivery enhancing compound reservoir. In some embodiments, the reservoir contains a volume of delivery enhancing compound in liquid form with the liquid reservoir in communication with an adsorbing or absorbing delivery enhancing compound source element. In other embodiments, the nicotine reservoir is or forms part of the delivery enhancing compound source element. A non-limiting example of such a combination source and reservoir would be a material (e.g., PE or PP) saturated with delivery enhancing compound solution. In particular embodiments, the reservoir provides sufficient delivery enhancing compound solution to enable a delivery device to provide therapeutically effective doses of nicotine over a desired time frame. Non-limiting examples would be devices capable of delivering sufficient delivery enhancing compound to enable delivery of 0-100 micrograms of nicotine per 35 cubic centimeter volume "puff" of gaseous carrier for a desired number of puffs per day (e.g. 200) over a desired number of days (e.g. 1-7 days). In certain embodiments, the amount of nicotine delivered is between 10 and 110, 20 and 100, 50 and 100, or 40 and 60 micrograms of nicotine per 35 cubic centimeter volume "puff." Embodiments delivering 0 micrograms of nicotine are generally intended to be the end points of a gradual nicotine cessation program.

Temperature

In some embodiments of the methods, the method involves a step of increasing the temperature of one or more of the gaseous carrier, the nicotine source and/or the enhancer source (when present). Such temperature control steps are generally used to regulate or to further enhance the amount of nicotine delivery. In some embodiments, the increase in temperature is used only if the nicotine levels delivered would generally be otherwise expected to drop below a desired minimum. In some embodiments this may be more than 20 micrograms, preferably more than 30 micrograms, and more preferably more than 40 micrograms of nicotine per 35 cc volume puff. For example, a common target delivery concentration is 40-50 micrograms nicotine per 35 cubic centimeter volume "puff" as measured by a well known technique in the nicotine delivery field. See The FTC Cigarette Test Method for Determining Tar, Nicotine and Carbon Monoxide Yield of U.S. Cigarettes: Report of the NCI Ad Hoc Committee. Smoking and Tobacco Control Monograph #7. Dr. R. Shopland (Ed.). Darby, Pa.: Diane Publishing Co, 1996. In some embodiments, generally a lower temperature is used first with the temperature increasing over time to sustain a desired nicotine delivery concentration from a nicotine source. In other embodiments a constant temperature is maintained during use. In some embodiments, the temperature is elevated to a maximum of 100 degrees C., a maximum of 70 degrees C., or the temperature is elevated to 40±5 degrees C. For example, pyruvic acid as a delivery enhancing compound may be heated to 40 degrees C. to facilitate sustained nicotine delivery over multiple puffs at a desired nicotine concentration range (e.g. 20-50 micrograms per puff). Temperature control may in some embodiments be effected by a temperature control element. Such elements may be any known mechanism capable of achieving the desired target temperature for the gaseous carrier, the nicotine and/or the delivery enhancing compound(s). Particular examples of temperature control elements are illustrated below in the exemplary devices provided.

Devices

The methods described herein are generally carried out using specially adapted delivery devices configured to carry out the methods described herein during device operation. One of skill in the art will be able to design and produce a variety of delivery devices using the foregoing guidance. The Inventors however provide herein a number of delivery device configurations to further illustrate the methods herein and their practical application by way of specific examples. The gaseous carrier delivered to a device user can include a therapeutically effective dose of nicotine for smoking cessation, harm reduction and/or substitution. Preferred delivery device embodiments are pulmonary delivery systems. Pulmonary delivery systems have the ability to deliver consistent doses with suitable particle-size and low particle-size variability to the deep lung. Of the various non-invasive drug delivery technologies available, including nasal, transdermal, buccal, and needle-free injections, pulmonary delivery offers unique potential for precise dose titration, rapid absorption, and high bioavailability to deliver novel therapeutics and improve delivery of existing compounds.

MODES FOR CARRYING OUT THE INVENTION

Screening for a Suitable Experimental Design for Nicotine Aerosol Formation

Several experimental designs were tested as described below to evaluate the generation of aerosol particles by allowing acid vapor to react instantly with base vapor.

Experiment #1: Hydrochloric Acid and Ammonia were Used to Generate a Mixture of Vapors in a "Y" Shaped Tube that was then Passed Over Nicotine Free Base Objective:

The aim was to evaluate the effectiveness of a chemically robust acid/base system to generate an aerosol of sufficient characteristics to aerosolize nicotine free base.

Experimental Design:

The experimental design included two identical glass test tubes (Tube A contained 5 ml of hydrochloric acid (HCl) and Tube B contained 5 ml ammonia ($NH_3$)) connected through a "Y" shape tube designed to allow for the vapors from the two test tubes to be admixed instantly in the "Y" shape tubing and then passed over nicotine free base using a Controlled Puff Volume Apparatus, CPVA (40 cc air at 2 seconds' duration (3-second interval) for 100 times (100 puffs)). The admixture of HCl and $NH_3$ vapors produced a white, dense and visible cloud.

Results:

TABLE 1

Amount of Nicotine Obtained After Passing HCl and $NH_3$ Over Nicotine

| Sample ID | Nicotine(μg)/sample | Nicotine(μg)/puff |
|---|---|---|
| HCl and $NH_3$ only | 0 | 0 |
| Nicotine, HCL and $NH_3$ | 3796.265 | 37.963 |
| Nicotine only | 1291.924 | 12.919 |

Discussion:

The use of hydrochloric acid, ammonia and nicotine resulted in significant nicotine delivery vs. nicotine only, as shown in Table 1. However, due to the chemical reactivity and corrosive nature of the acid and base chosen for this experiment, alternative constituents were evaluated that are more amenable to human use such as non-corrosive acid alternatives, including volatile and low-volatility organic acids (e.g., fatty acids).

Experiment #2: Screening for Suitable Acid Candidates for Use in the Development of Acid Over Nicotine Base Aerosol Delivery Arrangement Objective:

The objective of this experiment was to evaluate a series of acid candidates for their ability to admix with nicotine free base to form an aerosol suitable for pulmonary delivery. The superior candidates which created aerosols containing the greatest mass of nicotine free base reported as μg/puff were selected for further evaluation. Volatile carboxylic acids were selected as the organic acid of choice due to their relative high volatility and to the fact that they are constituents of cigarettes and other commercial products for human consumption such as food additives, flavoring agents and sweetening agents.

Experimental Design:

Two identical rectangular glass chambers measuring 4 cm×2 cm×1 cm each contained two inlet/outlet ports extending externally through the top of the chamber before turning 90° away from the center of the chamber. These ports were positioned on opposite sides and near the edge of the chambers. Internally, these ports consisted of a hollow glass tube that extended to near the bottom of the chamber. The purpose of these ports was to provide a controlled pathway for the movement of air across a volume of nicotine free base (chamber "B") or candidate acid (chamber "A"). For this experiment chamber B was filled with 200 μL nicotine free base and chamber A was filled with 200 μL pyruvic acid. The volumes of nicotine free base and pyruvic acid were added by Eppendorf pipette. Neat nicotine free base and neat pyruvic acid were stored at 4° C. and under Nitrogen gas. The working volumes of the nicotine free base and pyruvic acid were stored under refrigerated conditions but not under nitrogen. The working volumes were brought to room temperature before transferring to the chambers. A temperature probe was used to verify that the working volumes had reached room temperature. A filling portal was crafted into each chamber and positioned on the top center panel and was used for filling the chambers with the appropriate reactants. Once the appropriate volume was added to the individual chamber, the portal was sealed using a plug of PARAFILM® that was covered with TEFLON® tape. The chambers were then connected sequentially using TEFLON® tubing, secured by PARAFILM®. The outlet from Chamber B was then connected by TYGON® tubing to a filter holder containing a Cambridge filter (44 mm diameter) used to collect the reaction product. See Pillsbury H C, Smoking machine parameters for collection of total particulate matter and gases from low ignition-potential cigarettes. Under contract to the U.S. Consumer Product Safety Commission # CPSC-S-92-5472 I i Mar. 14, 1993. The opposing side of the filter housing was connected to a 100 cc syringe by TYGON® tubing. The syringe was affixed to an automated system making up the Controlled Puff Volume Apparatus (CPVA). For detailed methodology, See Levin E D, Rose J E and Behm F. Controlling puff volume without disrupting smoking topography. *Behavior Research Methods Instruments & Computers,* 21:383-386, 1989, the teachings of which are incorporated by reference herein. The total time to prepare the set-up from filling the first chamber to initiating the first sampling interval was approximately 5 minutes. The CPVA was programmed to pull a volume of 35 cc air at 2 seconds duration (30 second intervals) for 20 times (20 puffs). The filled chambers were immersed at half height into a water bath and were allowed to equilibrate at 70° C. for 10 minutes prior to sampling.

Prior to the evaluation of the candidate acids, a control experiment was conducted in which only the nicotine free base was kept in a chamber and nicotine vapors were pulled through a Cambridge filter for 20 times (20 puffs of 35 cc air in 2 seconds duration and 30 seconds puff interval). All the samples were quantified by Gas Chromatography (GC) utilizing a NPD (nitrogen phosphorous detector).

Results:

The following table shows the results of the acid screen as well as the control experiment. Results are reported by the amount of nicotine measured in each puff.

TABLE 2

Nicotine Delivery of Acid Over Base at ~70° c.

| Sample ID | Nicotine(μg)/puff |
|---|---|
| Nicotine Control | 46.12 |
| 4-Methyl-2-oxovaleric acid over Nicotine | 281.39 |
| Isovaleric acid over Nicotine | 25.00 |
| Caprylic acid (Octanoic acid) over Nicotine | 29.44 |
| 2-Oxooctanoic acid over Nicotine | 90.48 |
| Glycolic acid over Nicotine | 35.32 |
| Caproic acid over Nicotine | 14.97 |
| Levulinic acid over Nicotine | 39.93 |
| 2-Oxovaleric acid over Nicotine | 297.75 |
| Propionic acid over Nicotine | 09.68 |
| Pyroligneous acid over Nicotine | 32.54 |
| 2-Mercaptopropionic acid over Nicotine | 19.29 |
| 4-Pentenoic acid over Nicotine | 24.92 |
| 2-Nonenoic acid over Nicotine | 39.84 |
| Geranic acid over Nicotine | 40.54 |
| 3-Methyl-2-oxovaleric acid over Nicotine | 363.89 |
| 2-Methyl-4-pentenoic acid over Nicotine | 26.03 |
| 3-Cyclohexane-1-carboxylic acid over Nicotine | 48.24 |
| Glyoxylic acid over Nicotine | 35.17 |
| Lactic acid over Nicotine | 39.88 |
| Oleic acid over Nicotine | 48.45 |
| Trimethylpyruvic acid over Nicotine | 26.69 |
| Pyruvic acid over Nicotine | 362.28 |
| 3-Methyl-2-oxobutanoic acid over Nicotine | 213.99 |

Discussion:

The experimental results show that at approximately 70° C., 3-Methyl-2-oxovaleric acid over nicotine delivers the greatest amount of nicotine (363.89 μg/puff), followed by Pyruvic acid (362.28 μg/puff), 2-Oxovaleric acid (297.75 μg/puff), 4-Methyl-2-oxovaleric acid (281.39 μg/puff), 3-Methyl-2-oxobutanoic acid (213.99 μg/puff) and 2-Oxooctanoic acid 90.48 μg/puff. These candidates were evaluated under ambient conditions as described in the following experiment. 3-Methyl-2-oxovaleric acid, Pyruvic acid, 2-Oxovaleric acid, 4-Methyl-2-oxovaleric acid, 3-Methyl-2-oxobutanoic acid and 2-Oxooctanoic acid represent the genus of carboxylic acids termed "2-Keto acids" or "Alpha-Keto acids."

Experiment #3: Evaluation of Leading Acid Candidates Under Ambient Temperature Objective:

The objective of this experiment was to assess which of the leading acid candidates selected from the experiment described above will deliver the greatest amount of nicotine under ambient conditions.

Experimental Design:

The current experiment was carried out as described in the previous experiment except that the glass chambers were not immersed in a heated water bath, but sampled at ambient temperature. Individual experiments were carried out using the selected acid candidates: 3-Methyl-2-oxovaleric acid, Pyruvic acid, 2-Oxovaleric acid, 4-Methyl-2-oxovaleric acid, 3-Methyl-2-oxobutanoic acid and 2-Oxooctanoic acid. For each experiment a different acid was placed in Chamber A as in the previous experiment with nicotine free base in Chamber B. A nicotine free base control experiment was also conducted as in the previous experiment.

Results:

The following table shows the results of the assessment of the leading acid candidates sampled under ambient conditions. Results are reported as the amount of nicotine measured in each puff.

TABLE 3

Nicotine Delivery Using Selected Acids Over Base (Ambient Temperature)

| Sample ID | Nicotine(µg)/puff |
|---|---|
| Nicotine base control | 8.76 |
| 3-Methyl-2-oxovaleric acid over nicotine | 12.93 |
| Pyruvic acid over nicotine | 44.68 |
| 2-Oxovaleric acid over nicotine | 18.96 |
| 4-Methyl-2-oxovaleric acid over nicotine | 13.63 |
| 2-Oxooctanoic acid over nicotine | 04.46 |
| 3-Methyl-2-oxobutanoic acid over nicotine | 18.65 |

Discussion:

The data from ambient temperature shows that the Pyruvic acid is the superior candidate to form nicotine aerosol with the delivery of 44.68 µg/puff.

Experiment #4: Assessment of Leading Acid Candidates from the Previous 70° C. and Ambient Temperature Experiments (Experiment 2 and 3 Respectively) Utilizing the Prior Art Design for Aerosol Generation Objective:

The objective of this experiment was to compare the prior art configuration to the sequential orientation of acid and base to determine which yields higher nicotine delivery. The two leading acid candidates which generated similar nicotine delivery at 70° C. and one acid candidate which delivered the highest amount of nicotine under ambient temperature (from Experiments #2-3) were tested under 70° C. and ambient conditions, respectively.

Experimental Design:

In this experiment, two identical rectangular glass chambers exactly like those used in Experiment #2 were employed. Chamber A contained 200 μL of the leading acid and chamber B contained 200 μL of nicotine free base. The two chambers were connected via a "Y" shaped glass connector which was then connected to the same PTFE housing containing a Cambridge filter as described previously. The vapors from the tubes were allowed to be admixed instantly in the "Y" shaped glass connector upon pulling a volume of 35 cc air in 2 seconds duration (30 seconds interval) for 20 times (20 puffs) using a controlled puff volume apparatus (CPVA). For the elevated temperature experiments, the acid and nicotine chambers were immersed at half height into a water bath with a water temperature of approximately 70° C. The chambers were allowed to equilibrate for 10 minutes prior to sampling. For the ambient room temperature experiments, both the chambers were placed on a laboratory bench. The collected samples were analyzed for nicotine using Gas chromatography with a Nitrogen Phosphorous detector.

Results:

The following table shows the results of the assessment of the leading acid candidates sampled at an elevated temperature (approximately at 70° C.) and ambient conditions and employing prior art systems; also reported for comparison are the results using a sequential acid-over-base design (from Experiments #2-3). Results are reported as the mass of nicotine measured in each puff.

TABLE 4

Nicotine Delivery Using a "Y" Shaped Design (Prior Art)

| Sample ID | Nicotine(μg)/puff Prior Art (Y-Connector) | Nicotine(μg)/puff Sequential Design |
|---|---|---|
| At ~70° C. | | |
| 3-Methyl-2-oxovaleric acid and nicotine | 11.50 | 363.89 |
| Pyruvic acid and nicotine | 23.00 | 362.28 |
| At ambient room temperature | | |
| Pyruvic acid and nicotine | 3.26 | 44.68 |

Discussion:

Based on the current data the nicotine delivery in the prior art design is significantly lower than the sequential design and hence the sequential design is the superior method for the delivery of nicotine aerosol.

Experiment #5: Effectiveness of a Sequential Arrangement of an Acid Reservoir and a Base Reservoir to Provide an Acid Over Base Environment in the Development of an Aerosol Plume with Sufficient Concentrations of Nicotine Objective:

The objective of this experiment was to determine the influence of the arrangement of the acid and base reservoirs in sequence allowing the acid vapors to be lifted into the nicotine free base chamber and over the nicotine to generate a plume cloud with sufficient quantities of nicotine free base. Pyruvic acid was selected for use in this experiment.

Experimental Design:

The experimental design was the same as in Experiment #2. This experiment was divided into two parts, A and B. The first part, A, involved the assessment of the use of 200 μL each of nicotine free base and pyruvic acid in separate chambers collected over 3 samples (20 puffs per sample). The second part of the experiment (part B) involved a comparison of the above system tested under ambient and 40° C. conditions to evaluate the effect of mild heat on aerosol formation and nicotine delivery.

Results (Part A):

The following tables show the results of the pyruvic acid over nicotine free base experiment under ambient conditions (part A). Results are reported by the total mass of nicotine and the amount of nicotine measured in each puff.

TABLE 5

Nicotine Delivery of Acid Over Base

| Sample ID | Total Nicotine (μg)/sample | Nicotine (μg)/puff |
|---|---|---|
| Pyruvic acid over Nicotine free base-1 | 782.16 | 39.11 |
| Pyruvic acid over Nicotine free base-2 | 623.02 | 31.15 |

TABLE 5-continued

Nicotine Delivery of Acid Over Base

| Sample ID | Total Nicotine (µg)/sample | Nicotine (µg)/puff |
|---|---|---|
| Pyruvic acid over Nicotine free base-3 | 533.73 | 26.69 |
| | Mean (Coefficient of Variation (CV)) | 32.31 (19.5%) |

Discussion (part A):

These results indicate that there is an overall decline in nicotine yield from the first sample to the last, by about 32%.

Results (Part B)

The following tables show the results of the pyruvic acid over nicotine free base experiment at 40° C. Results are reported by the total mass of nicotine and the amount of nicotine measured in each puff.

TABLE 6

Nicotine Delivery of Acid Over Base at 40° C.

| Sample ID | Total Nicotine (µg)/sample | Nicotine (µg)/puff |
|---|---|---|
| Pyruvic acid over Nicotine free base-1 | 2341.09 | 117.05 |
| Pyruvic acid over Nicotine free base-2 | 2141.20 | 107.06 |
| Pyruvic acid over Nicotine free base-3 | 2137.92 | 106.90 |
| | Mean (CV) | 110.337 (5.3%) |

Discussion (Part B):

A 3 to 4 fold increase in the mass of Nicotine/puff was observed under heated conditions when compared to ambient conditions. Further, the coefficient of variation significantly improved to about 5% representing good control of the delivery dynamics. Moreover, there was no significant decline in nicotine delivery across puffs.

Experiment #6: Investigation of Nicotine Aerosol Formation and Delivery by Using the Sequential Set up with Pyruvic Acid in a Miniaturized/Cigarette Sized Device (8 cm Long and 8 mm ID)

Materials and Method

Matrix Materials Used:

Air-freshener wick samples made of a blend of PE and PP fibers (sold as X-40495 fiber from Porex Technologies) were used as a matrix upon which pyruvic acid was loaded and GORE™ Medical Membrane (pore size of 0.2 micron) consisting of an expanded PTFE medical membrane with a non-woven PET membrane support (sold as SMPL-MMT314 from W. L. Gore & Associates, Inc.) was used as a matrix to load nicotine free base. The membrane sheet was rolled into a straw configuration to provide a polyester inner wall and TEFLON® outer wall having approximate dimensions of 1.5 mm ID and cut into 4 cm long pieces.

Experimental Design:

A piece of air-freshener wick was loaded with 180 µL of pyruvic acid (pyruvic acid source element) and the inner walls (polyester side) of three pieces of the 4 cm long and 1.5 mm ID rolled medical membrane were coated with 90 µL (3×30 µL) of nicotine free base. The air freshener with loaded pyruvic acid was inserted into the distal end of 8 mm ID and 9 cm long clear TEFLON® tube and the three pieces of the medical membrane with nicotine free base were inserted tightly into a TEFLON® washer which had three holes (nicotine source element). The nicotine source element was inserted into the 9 cm long, 8 mm internal diameter (ID) TEFLON® tube with the pyruvic acid source element leaving a gap between the pyruvic acid source element and nicotine source element of 2 cm. The arrangement of the source elements was in such a way that a measured volume of air (35 cc at 2 sec duration and 30 second puff interval for 20 times) pulled by automated syringe pump traveled first through the pyruvic acid source element and then through the nicotine source element to form an aerosol. The proximal end of the device was connected to a controlled puff volume apparatus (CPVA) containing a Cambridge filter (to collect aerosol product). For the elevated temperature (40° C.) experiment, the 9 cm long device (which had both pyruvic acid and nicotine source elements) was completely immersed in a water bath and equilibrated for 10 minutes prior to sampling. The ambient condition experiment was carried out by placing the chambers on a laboratory bench.

Results:

The samples were analyzed for nicotine content and reported in Table 7 and Table 8.

TABLE 7

Nicotine Delivery in a Miniaturized Device Experiment at ~40°

| Sample ID | Nicotine (µg/puff) |
|---|---|
| Pyruvic acid in air-freshener wick over nicotine in three rolled pieces of medical membrane | 103.58 |

TABLE 8

Nicotine Delivery in a Miniaturized Device Experiment at Ambient Temperature

| Sample ID | Nicotine (µg/puff) |
|---|---|
| Pyruvic acid in air-freshener wick over nicotine in three rolled pieces of medical membrane | 29.20 |

Discussion:

The data indicates that when both the acid and base were loaded onto a matrix, in this case, air-freshener wick for acid and medical membrane for nicotine free base, a comparable nicotine delivery was obtained as with the previous experimental apparatus used in Experiment 5. In addition, the ~40° C. condition showed a significantly higher amount of nicotine delivery (approximately threefold) when compared to the ambient condition.

Exemplary Devices Adapted for Use with the Methods Herein

Delivery devices of some embodiments comprise a housing which simulates a tobacco smoking article. The housing may simulate the size, shape, and/or configuration of any article used for smoking tobacco articles. Non-limiting examples of smoking articles according to the present invention include cigarettes, cigars, cigarillos and pipes.

Delivery devices of some embodiments comprise a housing which simulates a pharmaceutical inhalation device. The housing may simulate the size, shape, and/or configuration of any pharmaceutical device used for inhalation. Non-limiting examples of pharmaceutical inhalation devices according to the present invention include, metered dose inhalers, pressurized metered dose inhalers, dry powder inhalers, nebulizers and liquid based inhalers.

Exemplary Device 1

Directing attention to FIG. 1, a device for the formation and delivery of a nicotine aerosol to a user according to an embodiment of the present invention is shown. Specifically, nicotine inhaler 10 having the size, shape, and appearance of a cigarette is shown. Nicotine inhaler 10 consists of housing 12, which has an elongated cylindrical shape and is hollow. To allow for a gaseous flow through inhaler 10, housing 12 contains gaseous inlet 14 and gaseous outlet 16 on opposing ends.

The portion of housing 12 between gaseous inlet 14 and gaseous outlet 16 is divided into three compartments capable of holding a first, second, and/or third substance. The first, second, or third substance can comprise a vapor forming medicament, such as nicotine.

Figure 2:
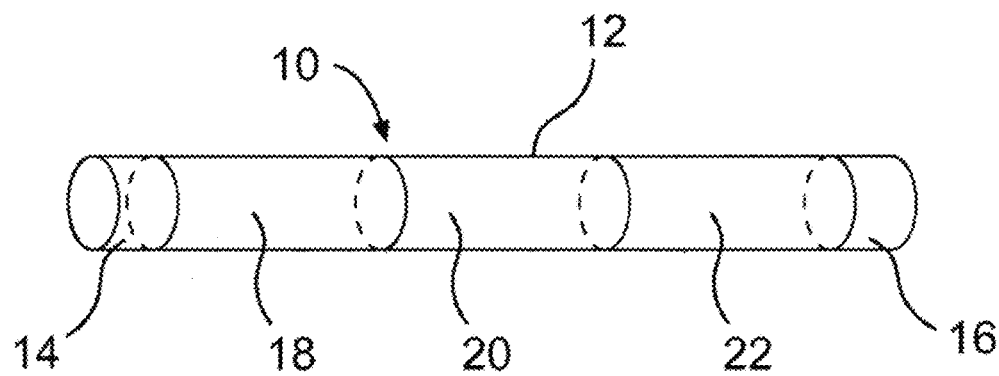
FIG. 2 a perspective view of the interior of an exemplary delivery device simulating a cigarette.

As illustrated in FIG. 2, nicotine inhaler 10 includes first compartment 18, second compartment 20, and third compartment 22. Nicotine, preferably in the free base form, may be placed in any of the three compartments. For example, nicotine can be placed within second compartment 20. A suitable delivery enhancing compound, such as an acid, is placed within first compartment 18. Any suitable acid can be used. For example, pyruvic acid can be placed within first compartment 18. Pyruvic acid is a volatile substance which has a substantial vapor pressure at room temperature. As such, any free space within first compartment 18 will be filled to some degree with pyruvic acid vapor, that is, gaseous pyruvic acid. Although the vapor pressure of nicotine is less than that of pyruvic acid, nicotine is also a volatile substance. In the same manner, any free space within second compartment 20 will be filled to some degree with nicotine vapor.

It should be appreciated that the pyruvic acid is held within first compartment 18 on a delivery enhancing compound source element (not shown) and nicotine is held within second compartment 20 on a nicotine source element (not shown). Additionally, a third substance may be held on a third source element (not shown) within third compartment 22. Furthermore, one or more of the source elements may be integral with or part of compartments 18, 20, and 22, respectively.

The delivery enhancing compound source element can be any size and shape that allows a gaseous stream to contact a vapor of the acid and pass through first compartment 18. The nicotine source element can be any size and shape that allows a gaseous stream to contact a vapor of nicotine and pass through second compartment 20. The third source element can be any size and shape that allows a gaseous stream to contact a third substance and pass through third compartment 22.

The delivery enhancing compound source element can be composed of any suitable material capable of holding the acid on its surface while allowing the acid vapors to permeate into the surrounding area. The nicotine source element can be composed of any suitable material capable of holding nicotine on its surface while allowing the nicotine vapors to permeate into the surrounding area. The third source element can be composed of any suitable material capable of holding a third substance. In specific embodiments, the suitable material holds the third substance on its surface while allowing the vapor of the third substance to permeate into the surrounding area.

Preferably, a suitable source element material is inert to any substance to be placed on its surface. Additionally, a suitable material is preferably adsorbing with respect to any substance to be placed on its surface such that said substance is adsorbed on the surface of the material. Although a material having both absorptive and adsorptive characteristics can be employed, a material capable of holding the delivery enhancing compound(s), nicotine and/or third substance through adsorption is preferred. Non-limiting examples include glass, aluminum, PET, PBT, PTFE, ePTFE, and BAREX®.

The adsorptive material may function via capillary action to continuously present the substances to the surface of the adsorbing material.

Third compartment 22 can contain a purifying agent. For example, activated charcoal can be incorporated into third compartment 22 using any method which provides the resulting third compartment 22 with gas purification capability. Suitable methods are well-known in the art. For example, the charcoal may be placed within third compartment 22 as a charcoal plug or filter.

Figure 3:
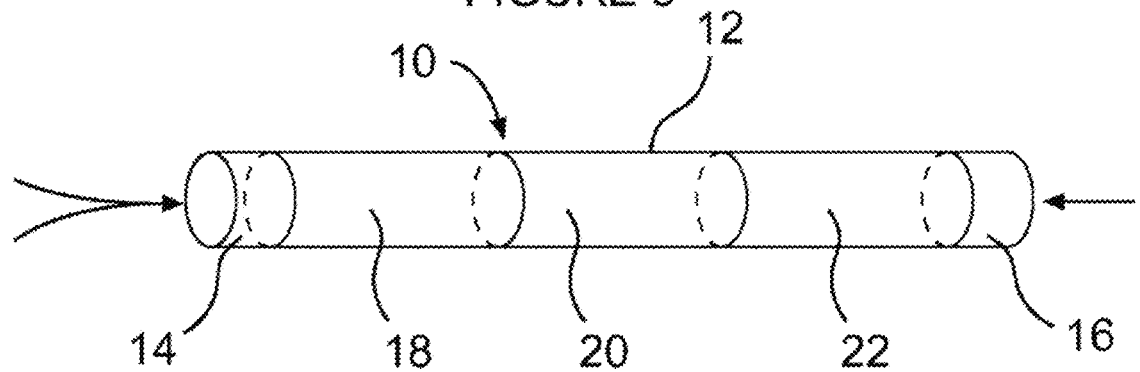
FIG. 3 a perspective view of the exemplary delivery device from FIGS. 1 and 2 in use.

In operation, a user puffs on gaseous outlet 16 of nicotine inhaler 10, as shown in FIG. 3. The partial vacuum created by the puffing action draws a gaseous stream into housing 12 through gaseous inlet 14. The gaseous stream enters first compartment 18 and captures a vapor of the acid by passing over the pyruvic acid source element held in first compartment 18. The gaseous stream that exits first compartment 18 and subsequently enters second compartment 20 is an acid-containing gaseous stream. The acid-containing gaseous stream generates a stream of nicotine-containing particles by passing over the nicotine held by the nicotine source element in second compartment 20. The stream of nicotine-containing particles passes through third compartment 22 and exits through gaseous outlet 16 into the mouth of the user. Any unreacted acid is removed from the stream of nicotine-containing particles via the activated charcoal filter in third compartment 22. It should be appreciated that pyruvic acid could be held on a first element in first compartment 18 and/or nicotine could be held on a second element in second compartment 20. Additionally, a third substance, such as a purifying or flavoring agent, may be held on a third element in third compartment 22. Furthermore, the first, second, and third elements may be integral with or part of compartments 18, 20, and 22, respectively.

Exemplary Device 2

Figure 4:
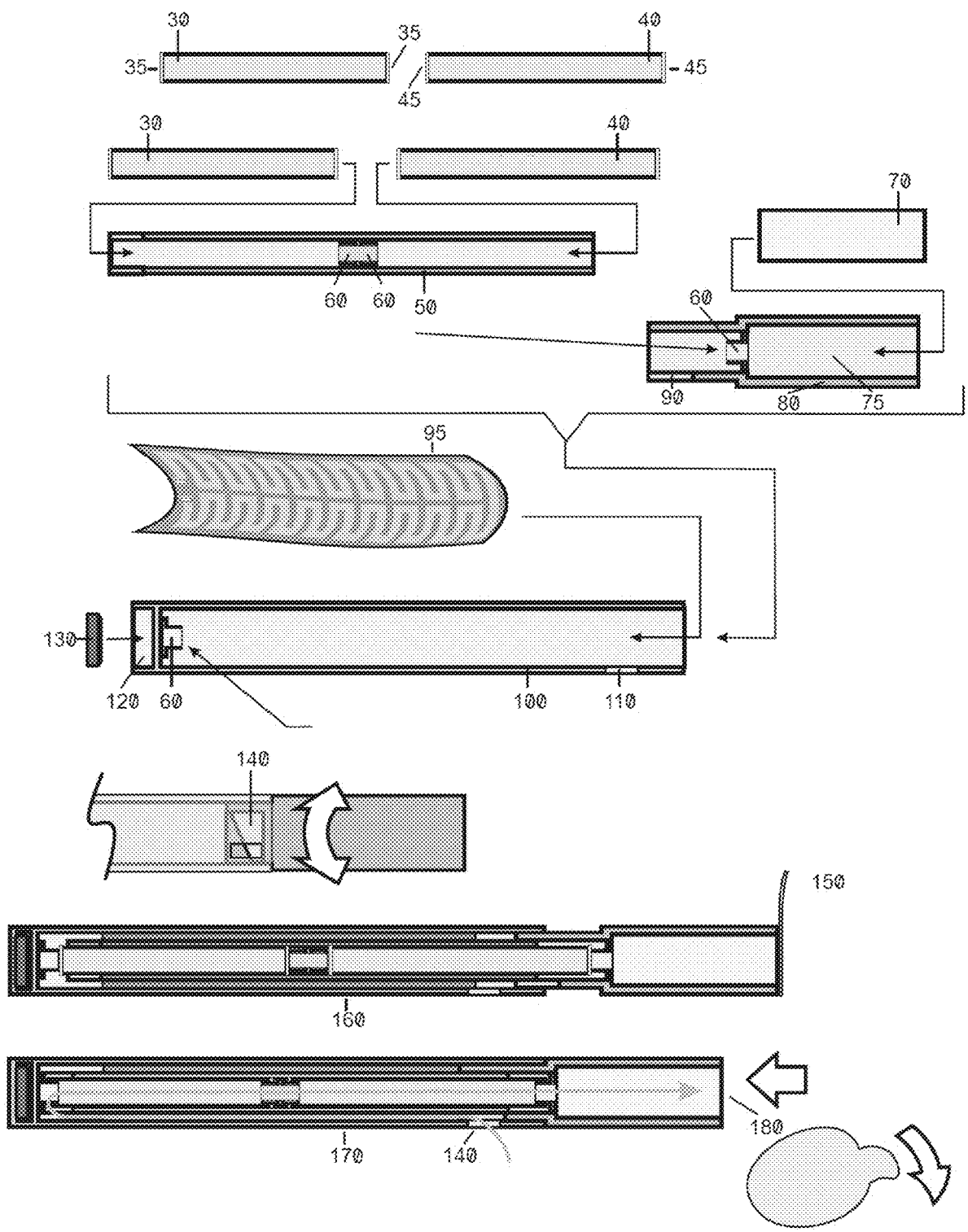
FIG. 4 a sectional view of the subcomponents of an exemplary delivery device showing the assembly stages and final configuration of the components for device use.

This exemplary device is illustrated and described by reference to FIGS. 4-6. In FIG. 4, the elements of the device are shown in an assembly flow chart. The delivery enhancing compound source 30 and the nicotine source 40 are optionally manufactured and stored as independent components generally having frangible barrier end caps 35 and 45 heat sealed on the ends. These two elements 30 and 40 are inserted into a first housing 50. First housing 50, containing delivery enhancing compound source 30 and the nicotine source 40, is then inserted into a second housing 100. The housings 50 and 100 and the elements 30 and 40 are generally extruded plastic tubing. Also inserted into second housing 100 is heating element 95. The heating element 95 is generally a thin flexible heating foil which is configured to wrap around housing 50 and to contact housing 50 sufficiently to enable heating the delivery enhancing compound source 30 and/or the nicotine source 40 to a desired temperature (e.g. 40 degrees C.). Heating element 95 is also adapted to contact battery 130 to supply power to the heating foil element 95.

Filter element 80 is adapted to insert and snap-lock into second housing 100. Filter element 80 comprises a filter cavity 75 adapted to contain a filter 70. Filter 70 is generally a charcoal filter and may contain additional volatile compounds such as flavoring agents commonly used in cigarettes. Filter element 80 may have foil seal 150 to seal the assembled pre-use configuration 160.

Filter element 80 has aperture 90 which aligns with aperture 110 of second housing 100. When assembled, air inlet 140 is formed. The filter element 80 and the second housing 100 are configured to permit rotation to select a desired air inlet 140 aperture dimension. The air inlet 140 forms when filter element 80 is fully inserted into second housing 100 as shown by 170. The full insertion of filter element 80 also forces penetrating elements 60 through frangible barriers 35 and 45 to unseal these elements for an unobstructed air flow pathway from air inlet 140 to particle delivery aperture 180.

Figure 5:
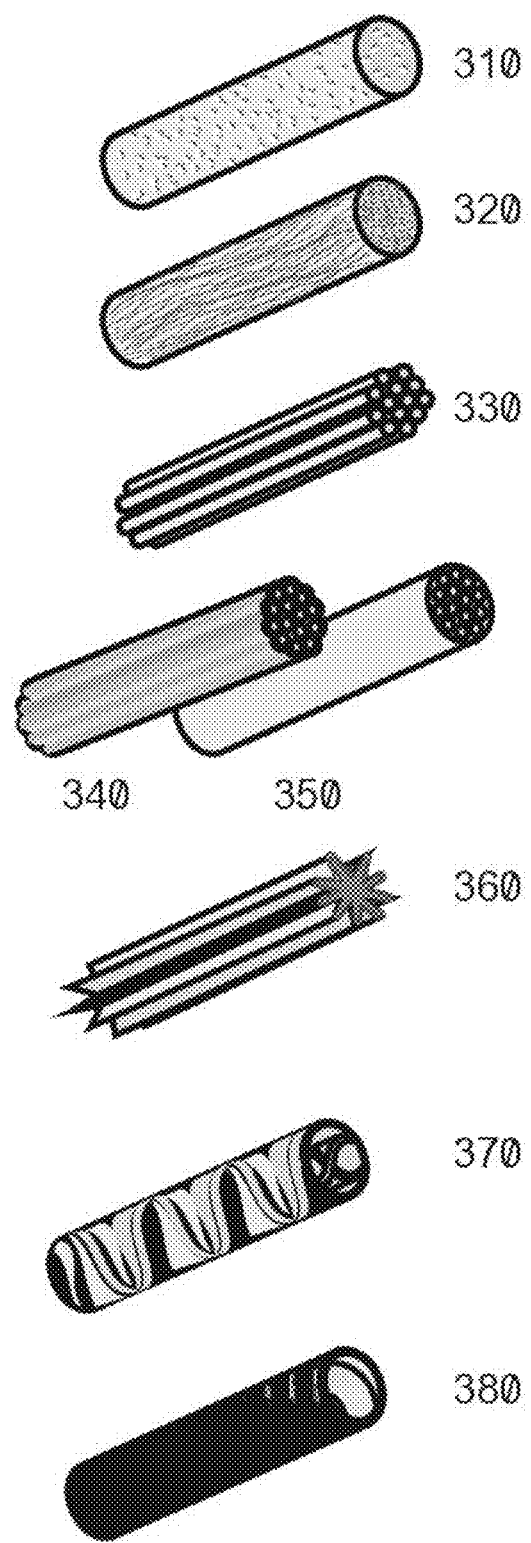
FIG. 5 a perspective view of various source elements for providing the nicotine or other medicament and the delivery enhancing compound.

FIG. 5 shows various alternative structures for delivery enhancing compound source 30 and the nicotine source 40. The delivery enhancing compound in this configuration is generally a volatile acid which may be held by adsorption onto sintered plug 310, PE wick 320, a fiber bundle 330, a mutilumen tube 340 or 350, woven or non-woven PET, PBT, or PETG fabric material 360, PET static mixer 370, or a helical path wrapped in nonwoven material 380.

Figure 6:
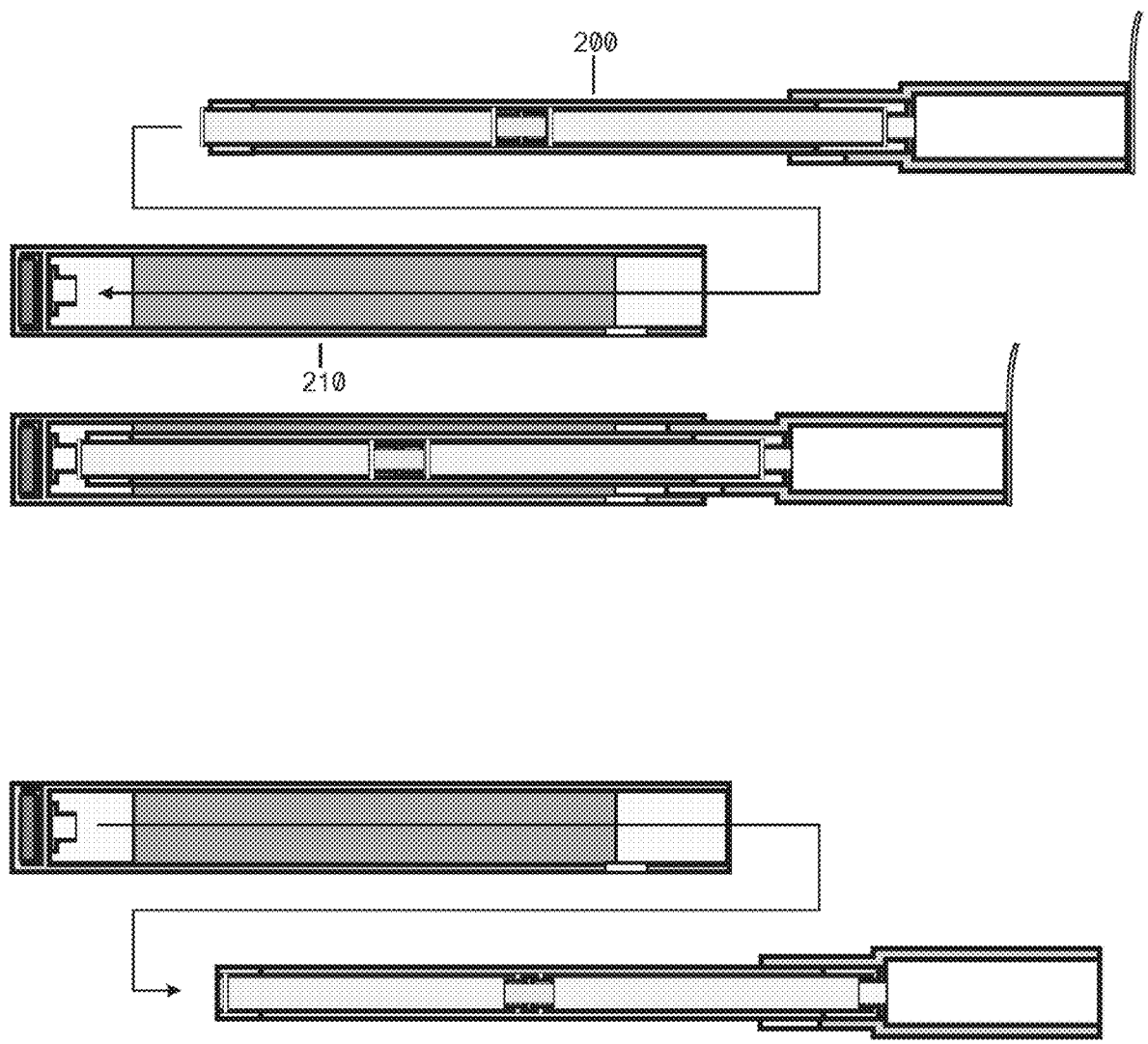
FIG. 6 a sectional view of the subcomponents of an exemplary delivery device showing reusable and disposable portions.

FIG. 6 shows some embodiments of this device where the device comprises a reusable portion 210 and a disposable portion 200. Referring to FIG. 1, disposable portion 200 comprises the delivery enhancing compound source 30 and the nicotine source 40, the first housing 50, and the filter element 80. The reusable portion 210 comprises second housing 100, heating element 95 and battery 130.

Exemplary Device 3

Figure 7:
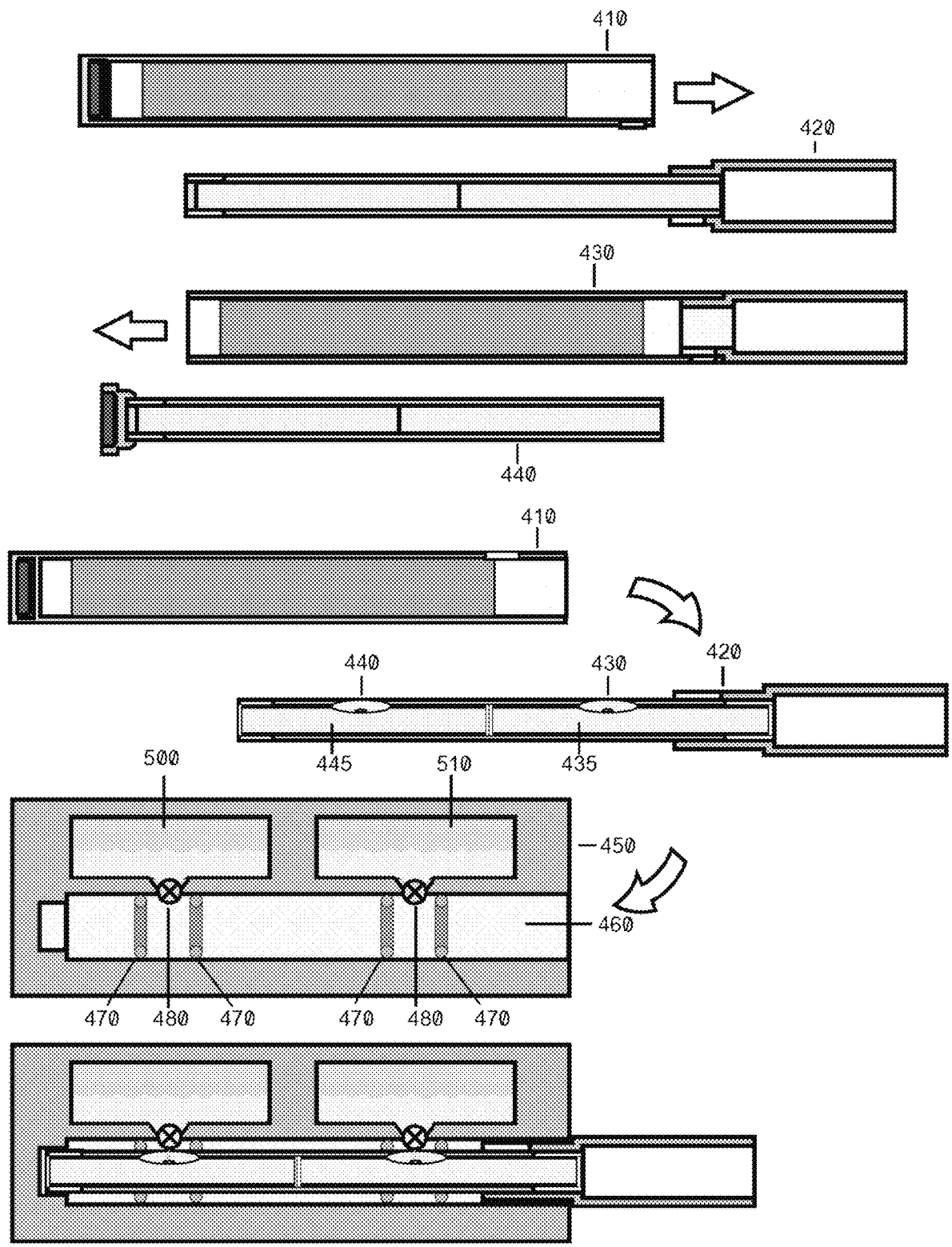
FIG. 7 a sectional view of the subcomponents of a reusable exemplary delivery device showing the device and a recharging unit for supplying nicotine or other medicament and the delivery enhancing compound.

A fully reusable exemplary device is illustrated by FIG. 7. Two alternative configurations are illustrated wherein portion 410 and 420 or 430 and 440 are reversibly attachable. For example the portions may be extruded plastic adapted and dimensioned to permit repeated snap-locking and removal. The removable portions 420 or 440 comprise apertures 430 and 440 for communication with delivery enhancing compound source 445 and nicotine source 435. Portions 420 or 440 insert into recharging element 450 through aperture 460. Elements 470 are sealing o-rings to seal off the reservoir when recharging delivery enhancing compound source 445 and nicotine source 435. Loading apertures 480 and 490 are configured to communicate with delivery enhancing compound source 445 and nicotine source 435 once portion 420 is seated in recharging element 450. In some embodiments, gravity drives flow from delivery enhancing compound reservoir 500 and nicotine reservoir 510 to delivery enhancing compound source 445 and nicotine source 435, respectively. In some embodiments, the flow from the reservoirs to the sources is in part due to wicking of the reservoir liquid by the source elements. For example, delivery enhancing compound source 445 and nicotine source 435 may comprise a source element containing PET to create rapid wicking and thus reloading of sources 445 and 435.

Exemplary Device 4

Figure 8:
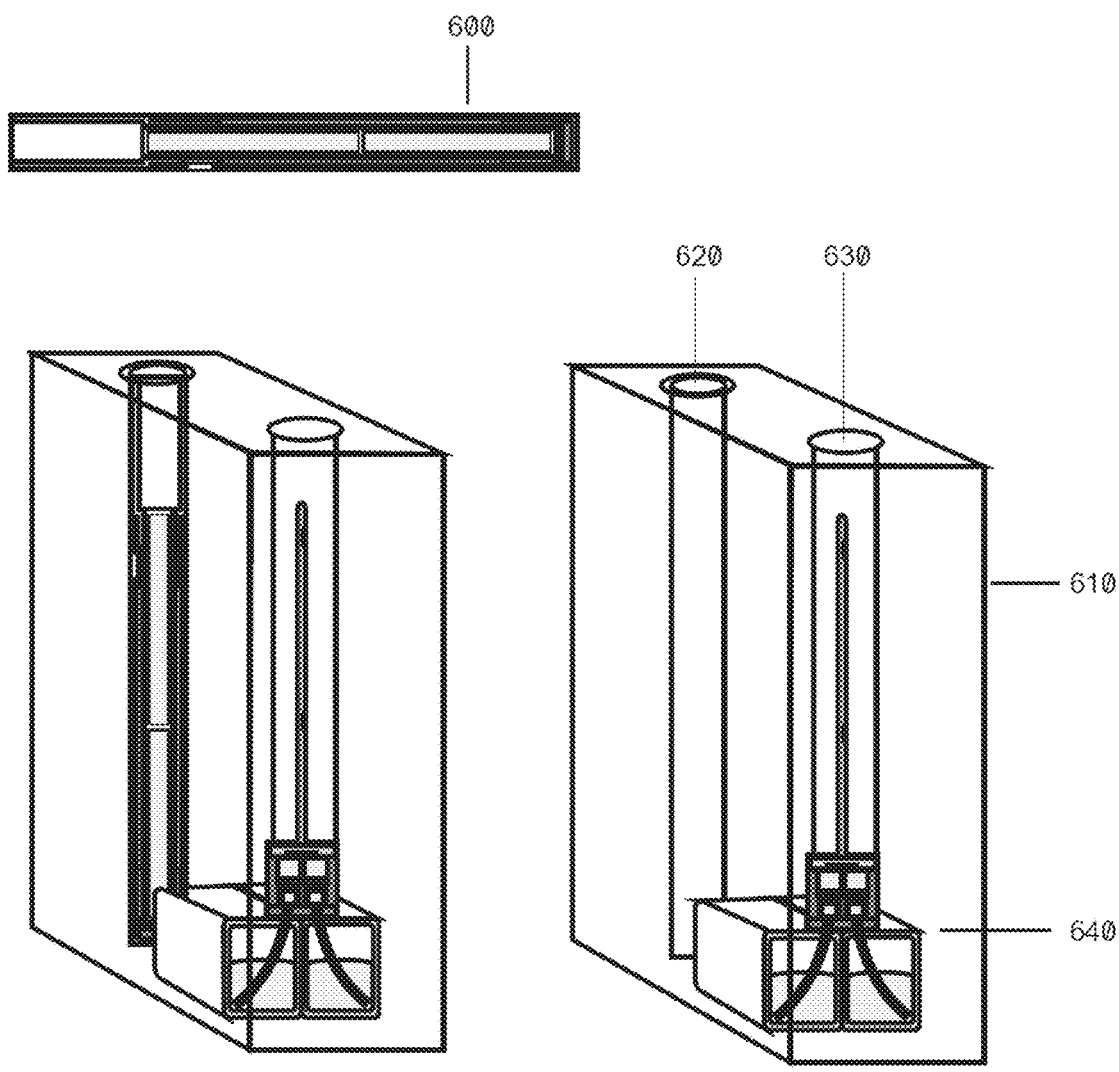
FIG. 8 a sectional view of a reusable exemplary delivery device showing the device and a perspective view of a recharging unit for supplying nicotine or other medicament and the delivery enhancing compound.
Figure 9:
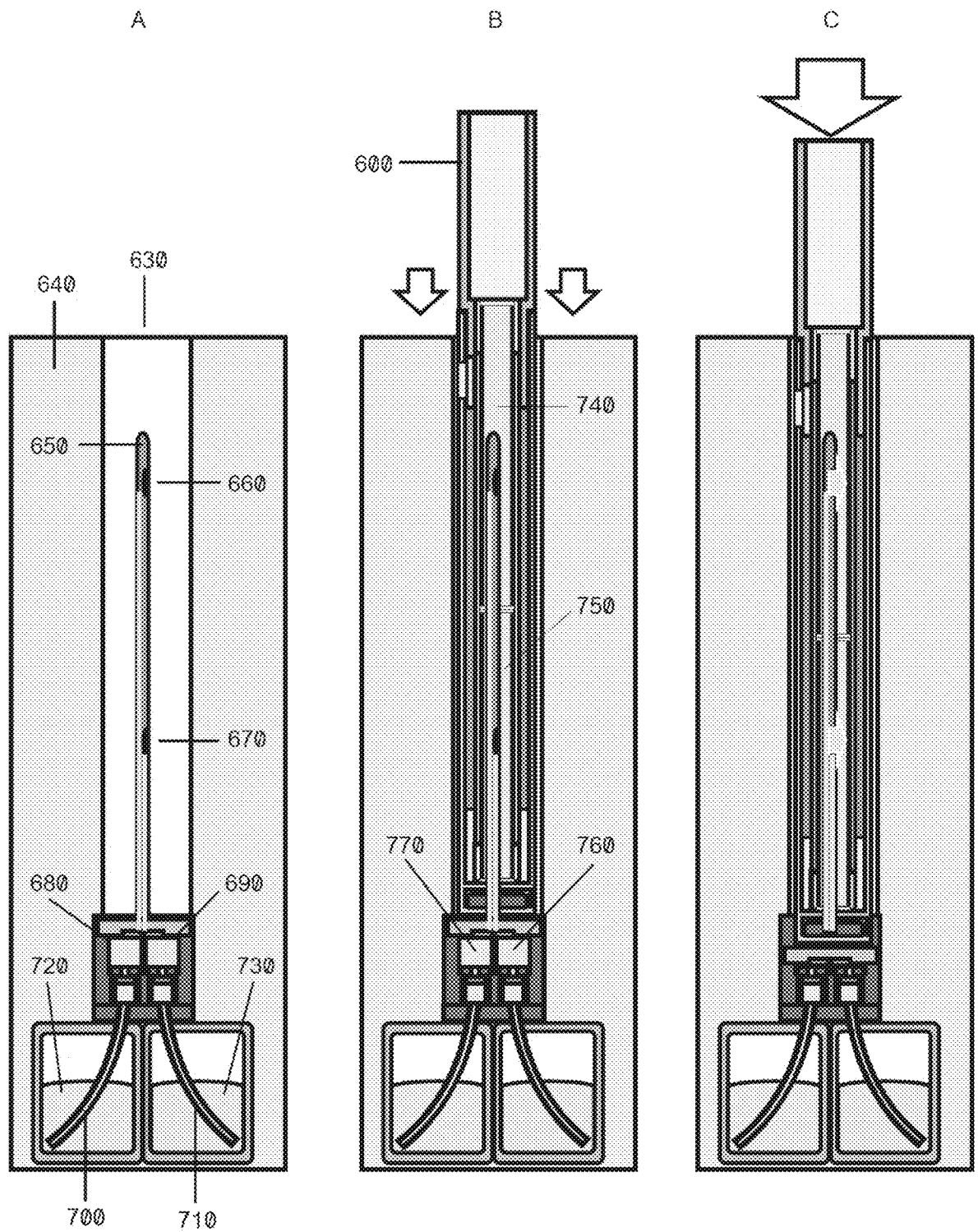
FIG. 9 a sectional view of a reusable exemplary delivery device showing the device and a recharging unit; 9A shows the recharging unit alone, 9B shows the delivery device seated in the recharging unit and 9C shows the delivery device after compression of the metered dose pumps of the recharging unit for resupplying nicotine or other medicament and the delivery enhancing compound.

Another exemplary device is illustrated by FIGS. 8 and 9. This exemplary device is rechargeable and configured to simulate a typical cigarette pack. Referring to FIG. 8, delivery device 600 is configured to insert into recharging unit 610 through storage aperture 620 and recharging aperture 630. When fully seated in the recharging unit 610 on recharging element 640, the device 600 is recharged with delivery enhancing compound and/or nicotine.

FIG. 9 shows the recharging element 640 in detail. In FIG. 9A, injection element 650 having loading apertures 660 and 670 is in flow communication with reservoirs 720 and 730 through metered dose actuator pumps 680 and 690 and tubes 700 and 710. In FIG. 9B, delivery device 600 is shown seated in recharging unit 640. Injection element 650 passes through a recharging aperture at the base of the delivery device and into said device so that apertures 660 and 670 are in communication with nicotine source element 740 and delivery enhancing compound source element 750. In FIG. 9C, the delivery device 600 is further inserted into recharging unit 640 to actuate the pumps 680 and 690 to deliver metered doses 770 of nicotine and 760 of delivery enhancing compound through apertures 660 and 670, respectively, and into nicotine source element 740 and delivery enhancing compound source element 750, respectively.

Exemplary Device 5

Figure 10:
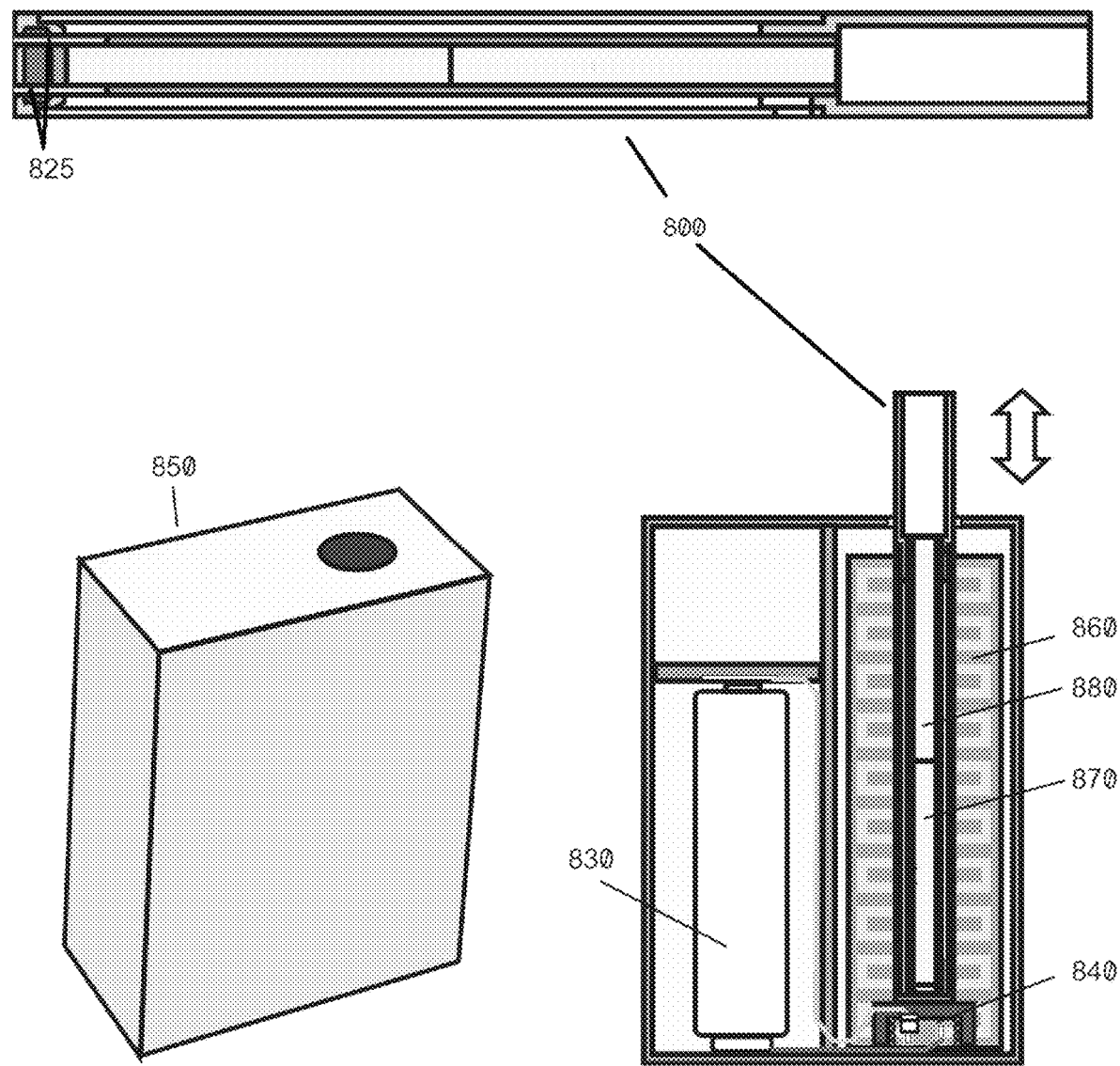
FIG. 10A a sectional view of an exemplary delivery device with a heating component therein shown in perspective view as a separate component; 10B an exemplary delivery device having an external heating unit into which the delivery device is seated for temperature control of the device and/or its constituents.

This exemplary device is illustrated by FIG. 10. This device configuration has a heating unit 850 external to the delivery device 800. Upon insertion of delivery device 800 into heating unit 850, electrical contacts 840 are in contact with leads 825 which permit battery 830 to heat foil heating element 860 to control the temperature of the delivery enhancing compound source 870 and nicotine source 880 to, e.g., 40±5 degrees C. An alternative configuration places the heating foil 860 within the delivery device 800, as shown in FIG. 4.

Exemplary Device 6

Figure 11:
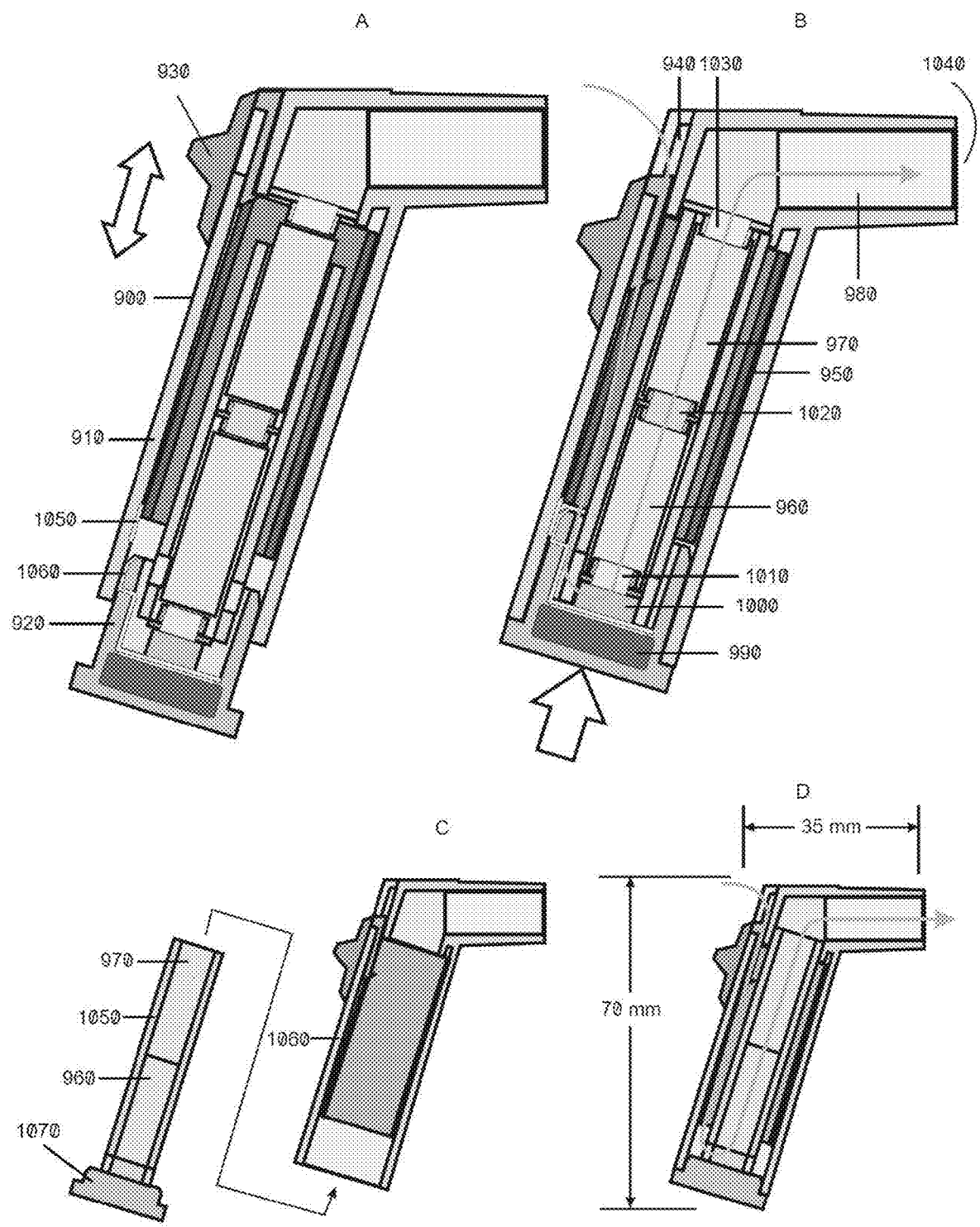
FIG. 11 a sectional view of an exemplary device simulates a metered dose inhaler commonly used for pharmaceutical delivery of inhaled medicaments.

The foregoing exemplary devices are generally configured to simulate a cigarette and cigarette pack. The delivery devices suitable for use with the methods herein are readily configured in a variety of ways. An example is illustrated in FIG. 11. This exemplary device simulates a metered dose inhaler commonly used for pharmaceutical delivery of inhaled medicaments. Delivery device 900 comprises a first housing 910 and a second housing 920. Second housing 920 is removable (FIG. 11A) and in (FIG. 11B) for recharging or replacement of battery 990. The in position brings electrical contact 1050 and 1060 into communication thereby allowing battery 990 to heat foil heating element 950 to in turn control the temperature of delivery enhancing compound source 960 and nicotine source 970. Air intake actuator 930 is configured to slide anywhere from the position in FIG. 11A to 11B. Power for heating foil element 950 may be optionally turned on or off using air intake actuator 930 or a separate switching means (not shown). Air intake aperture 940 may then be opened to a selected degree thereby controlling the volume of air per inhalation and consequently the amount of nicotine. This feature is analogous to adjustable air intake aperture 140 of FIG. 1. In operation, air is drawn through air intake aperture 940, down to chamber 1000, through conduit 1010, through the delivery enhancing compound source 960 where delivery enhancing compound is captured in the air flow. For example, pyruvic acid vapor may be emanating from a PET source element having liquid pyruvic acid adsorbed thereon. This vapor is moved by the air flow through conduit 1020 into the nicotine source 970. Here the delivery enhancing compound increases the concentration of nicotine in the airflow relative to the amount of nicotine vapor that would be contained in the same volume of air flow in the absence of the delivery enhancing compound. In the case of pyruvic acid, nicotine pyruvate salt particulates may be formed to enhance delivery of nicotine to a subject. Delivery may be further enhanced by elevating the temperature of, e.g., pyruvic acid and nicotine, by means of heating element 950 to increase the vapor pressure of those compounds. The airflow containing nicotine now moves through conduit 1030, through charcoal filter 980 and out the inhalation aperture 1040.

FIGS. 11C and D illustrate an embodiment of the exemplary inhaler device 900 wherein a portion of the device having the delivery enhancing compound source 960 and nicotine source 970 in a disposable housing 1050 which is configured to slide into and out of reusable housing 1060 to form a device functionally identical to device 900. Battery housing element 1070 is detachable from disposable element 1050 and thus reusable with portion 1060 and a replacement element 1050.

Exemplary Device 7

Figure 12:
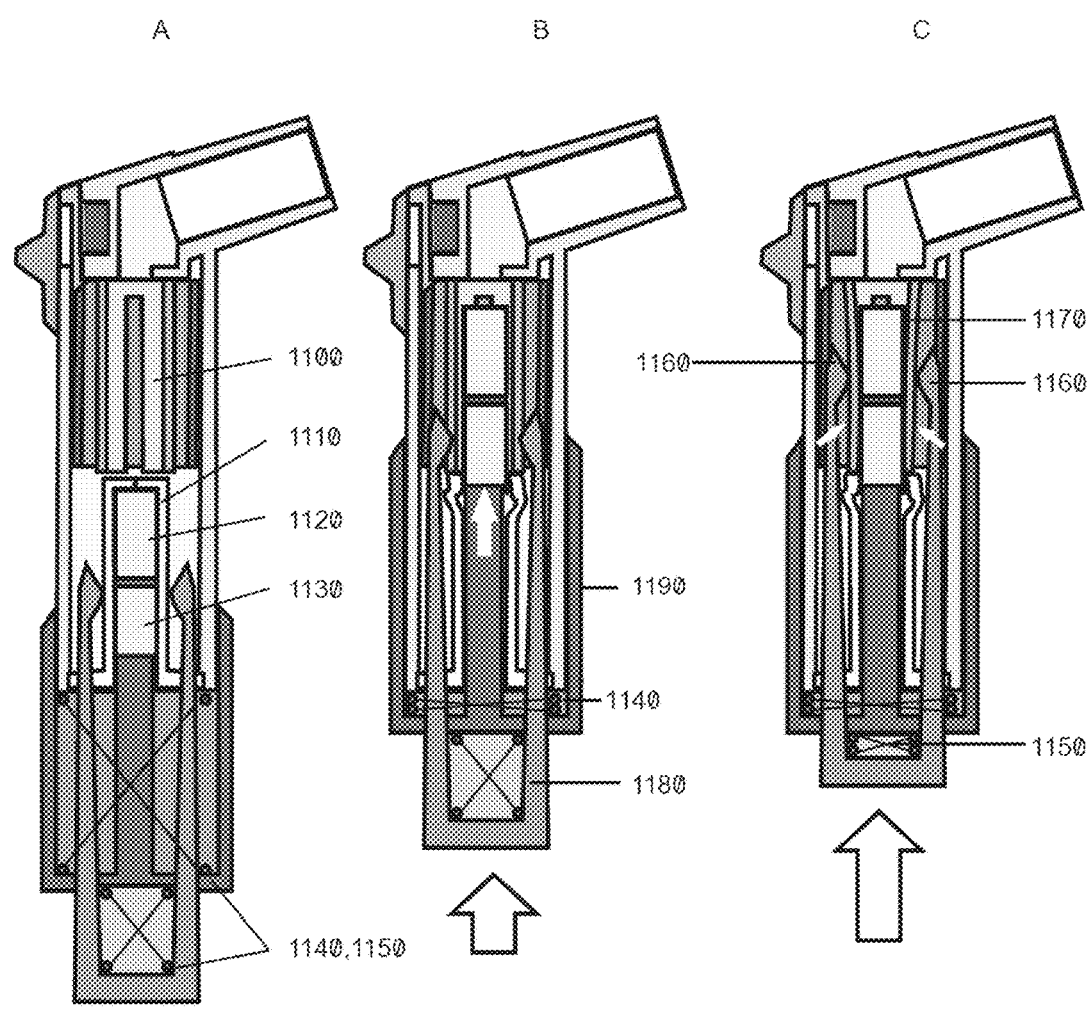
FIG. 12 a sectional view of an exemplary device simulates a metered dose inhaler commonly used for pharmaceutical delivery of inhaled medicaments.

FIG. 12, A-C illustrates another configuration of an inhalation device. In this configuration, the delivery enhancing compound source and the nicotine source are the lower and upper surface areas of split inner tube 1100. In the usage configuration 12A, an impermeable cover 1110 is in place over nicotine reservoir 1120 and delivery enhancing compound reservoir 1130. The impermeable cover 1110 reduces evaporative loss from the reservoirs and physically separates the reservoirs from the split inner tube 1100. In use, bottom housing 1180 is pushed into main housing 1190 until first catch spring 1140 is locked in the position shown in 12B. This places the reservoirs 1120 and 1130 in parallel proximity to the split inner tube 1100. Shown in 9C, the bottom housing 1180 is further inserted into main housing 1190 until second catch spring 1150 is locked in the position shown in 12C. In this third position, pressure elements 1160 squeeze split inner tube 1100 to force wall 1170 into contact with reservoirs 1120 and 1130. This action forces nicotine and delivery enhancing compound (e.g. pyruvic acid) onto the inner surface of wall 1170 to recharge this surface as the nicotine source and the delivery enhancing compound source.

Exemplary Device 8

Figure 13:
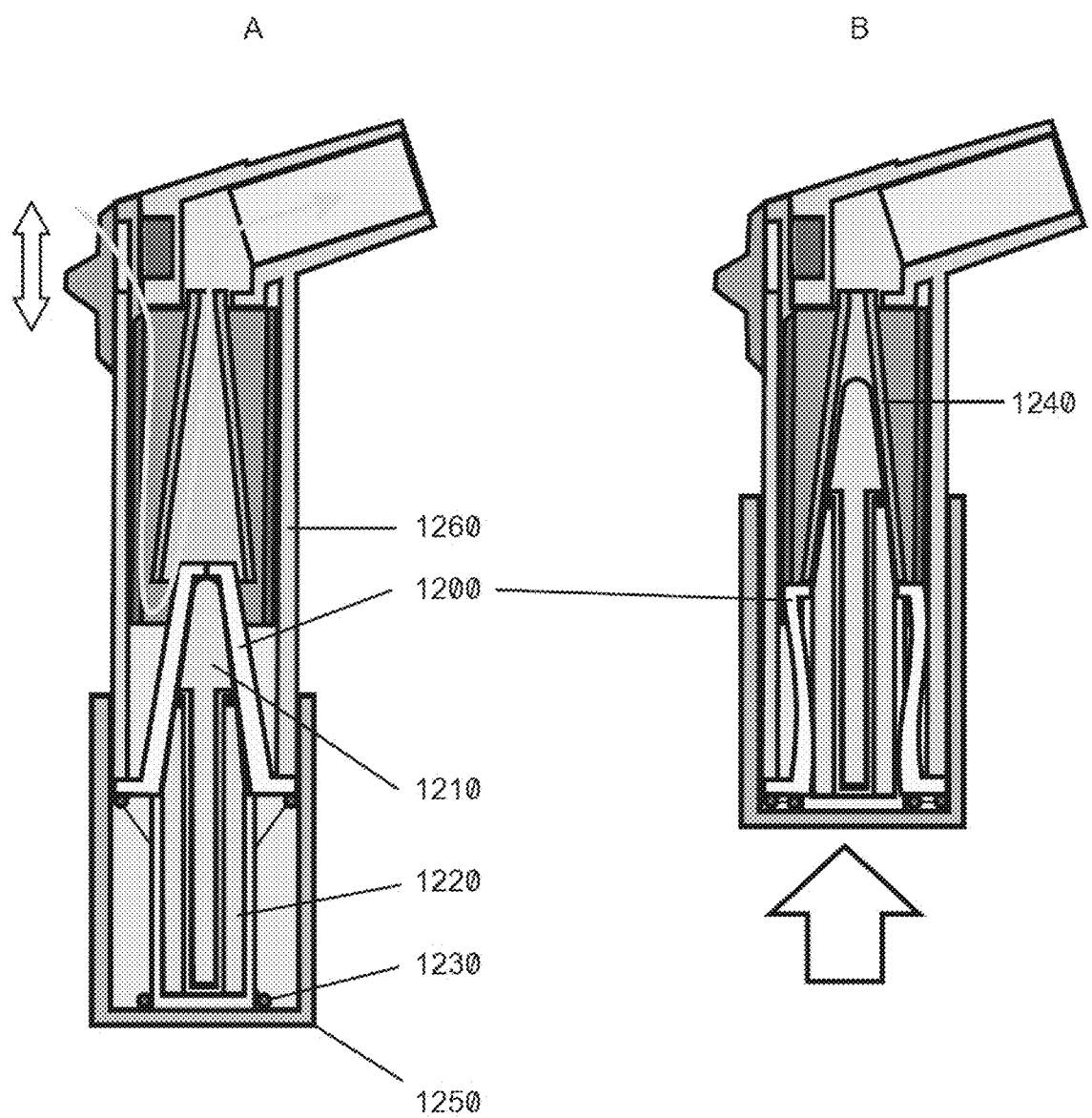
FIG. 13 a sectional view of an exemplary device simulates a metered dose inhaler commonly used for pharmaceutical delivery of inhaled medicaments.

FIG. 13 shows a variant of the device of FIG. 12. In this version, bottom housing 1250 is depressed against conical spring 1230 to force the nicotine reservoir 1210 and the delivery enhancing compound reservoir 1220 through reservoir cover 1200 and into contact with the inner surface of conical inner tube 1240, thereby coating the surface with nicotine and delivery enhancing compound (FIG. 13B).

Exemplary Device 9

Figure 14:
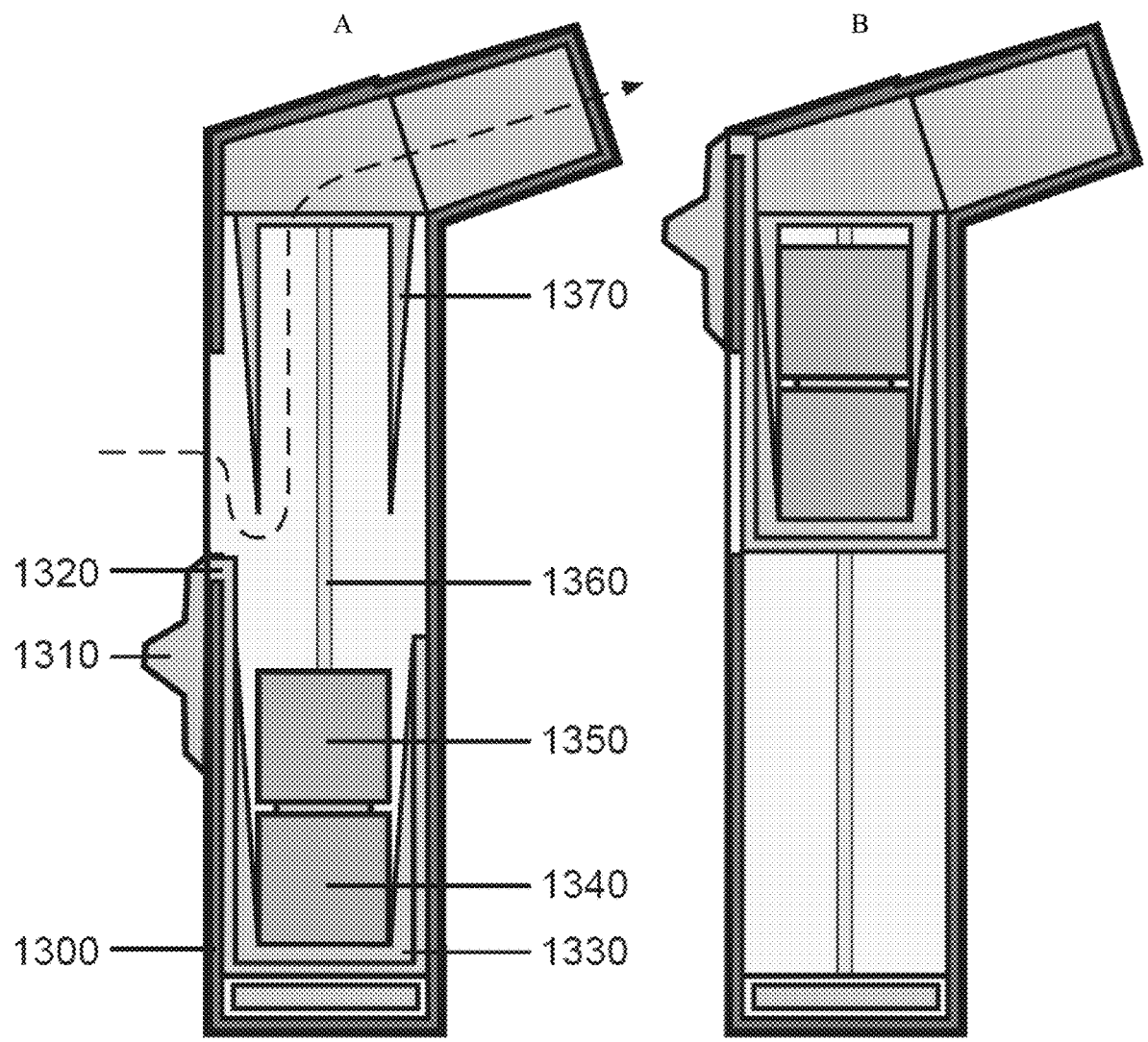
FIG. 14 a sectional view of an exemplary device simulates a metered dose inhaler commonly used for pharmaceutical delivery of inhaled medicaments.

FIG. 14 shows another version of the device of FIG. 12. In this version, outer housing 1300 is contiguous with the moving components being switch 1310 and the various internal elements shown. Switch 1310 is connected to source seating element 1330 by a connecting bar 1320. As switch 1310 is moved up, rigid seating element 1330 moves along pole 1360. At the charging position, reservoir elements 1340 and 1350 are brought into contact with flexible element 1370 which is also brought into contact with rigid seating element 1330. Rigid seating element 1330 is dimensioned to squeeze flexible elements 1370 into contact with reservoir elements 1340 and 1350 in the final portion of the sliding motion (FIG. 14B). This action coats the upper portion of flexible element 1370 with, e.g., nicotine base solution from reservoir 1350 and the lower portion of flexible element 1370 with pyruvic acid from 1340 to create a nicotine source and a delivery enhancing compound source, respectively. The top surface of reservoir 1350 may be covered by an impermeable material to limit the amount of volatilization of medicament and delivery enhancing compound from the reservoirs when in the operational position (FIG. 14A). A circular flap of flexible, impermeable material may extend from elements 1320 or 1330 to close off the volume below reservoir 1350 and further limit volatilization. In charging position (FIG. 14B) the flap would be forced down and away from the reservoirs by flexible element 1370.

Exemplary Device 10

Figure 15:
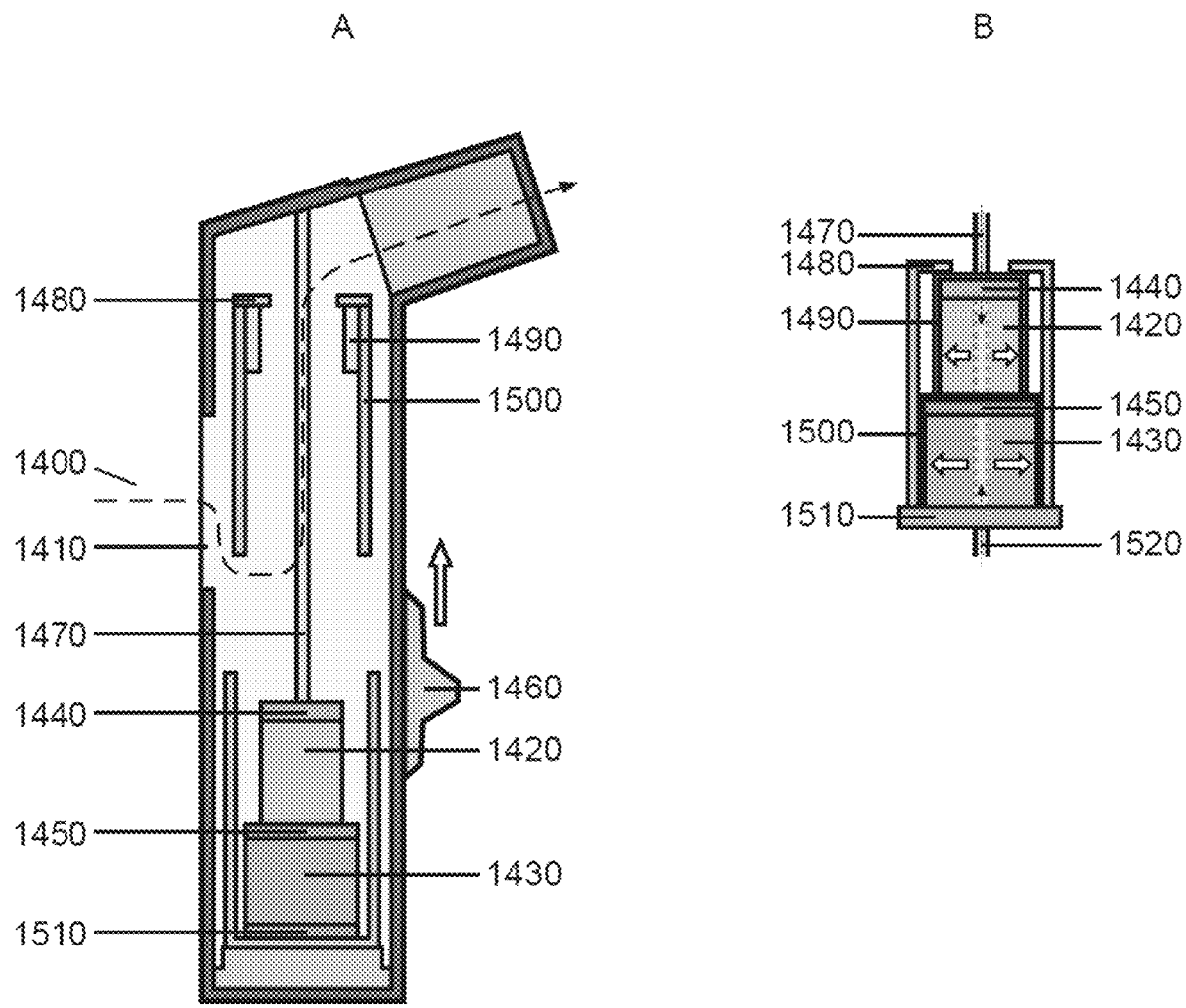
FIG. 15 a sectional view of an exemplary device simulates a metered dose inhaler commonly used for pharmaceutical delivery of inhaled medicaments.

FIG. 15 shows another delivery device configuration. FIG. 15A shows the device 1400 in use mode. Air moves from intake 1410 past delivery enhancing compound source 1500, nicotine source 1490 and through outlet 1415. The nicotine and delivery enhancing compound are coated onto the side walls of their respective sources. To recharge the sources, delivery enhancing compound reservoir 1430 and nicotine reservoir 1420 are provided. Switch 1460 may be actuated to recharge the sources. Upon activation by switch 1460, base 1510 is moved along guide rod 1470 toward delivery enhancing compound source 1500 and nicotine source 1490. Shown in FIG. 15B, upon contact with the delivery enhancing compound source 1500, the nicotine source 1490 and the upper stop element 1480, impermeable caps 1440 and 1450 compress reservoirs to force delivery enhancing compound and nicotine out onto the surfaces of the sources 1490 and 1500. The reservoirs in this device may be made of any flexible adsorbing or absorbing material capable of holding the nicotine or delivery enhancing solutions. The reservoirs will generally be motivated back down guide pole 1470 automatically after recharging the sources, thus making the device a conveniently operated "one click" device. The movement of the reservoirs may be achieved by any convenient means. For example, a motive wire 1520 may be provided within a groove on guide pole 1470. The motive wire 1520 may be attached to base 1510 and moves up and down the guide pole 1470 by a motor rotated element (not shown). In some versions of this device configuration, the top outer portion of device 1400 may be rotated to define the size of inlet 1410 analogous to element 140 shown in FIG. 4.

INDUSTRIAL APPLICABILITY

The methods and devices herein are useful for the therapeutic delivery of nicotine for smoking cessation, harm reduction and/or substitution. In addition, the devices and methods herein are useful as an alternative, general nicotine delivery system in place of tobacco based products. The methods and devices herein are further useful for the delivery of other medicaments as described herein.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

All references and other information cited to, or otherwise identified herein, are hereby incorporated by reference in their entireties as if each had been separately so incorporated. The priority application, U.S. provisional patent application Ser. No. 60/909,302 filed 30 Mar. 2007, is also hereby incorporated by reference in its entirety.

What is claimed is:

1. A device for delivering nicotine to a subject, the device comprising a housing, the housing comprising:
an inlet and an outlet in communication with each other and adapted so that a gaseous carrier may pass into the housing through the inlet, through the housing and out of the housing through the outlet, the device comprising in series from inlet to outlet;
a first internal compartment in communication with the inlet, the first internal compartment comprising a delivery enhancing compound source and a first frangible barrier end cap, wherein the delivery enhancing compound source further comprises a delivery enhancing compound, and wherein the delivery enhancing compound further comprises a carboxylic acid;
a second internal compartment in communication with the first internal compartment, the second internal compartment comprising a liquid nicotine source wherein the liquid nicotine source is a chemical capable of providing a volatile form of nicotine, the carboxylic acid reacting with the liquid nicotine source to form salt particles; and
a penetrating element constructed to penetrate the first frangible barrier end cap to form an air flow pathway, the first internal compartment and second internal compartment being arranged sequentially such that the gaseous carrier from the inlet first passes through the first internal compartment and then through the second internal compartment.

2. The device of claim 1 wherein the delivery enhancing compound source further comprises an adsorption element with the delivery enhancing compound adsorbed thereon and/or wherein the liquid nicotine source further comprises an adsorption element with nicotine adsorbed thereon.

3. The device of claim 2 wherein the adsorption element or elements comprises at least one from a group consisting of glass, aluminum, Polyethylene Terephthalate, Polybutylene Terephthalate, Polytetrafluoroethylene, and Expanded Polytetrafluoroethylene.

4. The device of claim 1, further comprising a first reservoir containing a volume of the delivery enhancing compound in liquid form, the first reservoir being in communication with the first internal compartment.

5. The device of claim 4, further comprising a second reservoir containing a volume of the nicotine in liquid form, the second reservoir being in communication with the second internal compartment.

6. The device of claim 1, comprising a third internal compartment in communication with the second internal compartment.

7. The device of claim 6, wherein the third internal compartment comprises a purifying agent.

8. The device of claim 6, wherein the third internal compartment comprises a flavoring agent.

9. The device of claim 6, where the third internal compartment comprises a medicament other than a liquid nicotine source.

10. The device of claim 9, wherein the medicament comprises a source of liquid nicotine.

11. The device of claim 1, wherein the housing simulates a tobacco smoking product.

12. The device of claim 11, wherein the tobacco smoking product simulates a cigarette.

13. The device of claim 1, wherein the housing simulates a pharmaceutical inhalation device.

14. The device of claim 1, wherein the liquid nicotine source comprises free base nicotine.

15. The device of claim 1, wherein the gaseous carrier is ambient air.

16. The device of claim 1, wherein the device further comprises a heating element configured to heat the delivery enhancing compound source and/or the nicotine source.

17. The device of claim 1, wherein the carboxylic acid comprises a 2-keto acid.

18. The device of claim 1, wherein the housing has a longitudinal axis with the outlet disposed at one end along the longitudinal axis, wherein the first internal compartment and second internal compartment comprise tubular sections of the housing, and wherein the first internal compartment and second internal compartment are arranged in an end-to-end relationship.

19. The device of claim 1, wherein the second internal compartment comprises a second frangible barrier end cap, the device further comprising one or more penetrating elements constructed to penetrate the first and second frangible barrier end caps to form an air flow pathway from the inlet to the outlet.

20. The device of claim 6, wherein the third internal compartment comprises a filter.

21. The device of claim 4, wherein the delivery enhancing compound source in the first internal compartment is configured to be loaded with delivery enhancing compound in liquid form from the first reservoir through a first loading aperture.

22. The device of claim 5, wherein the nicotine source in the second internal compartment is configured to be loaded with nicotine in liquid form from the second reservoir through a second loading aperture.

23. The device of claim 16, wherein the heating element is a flexible heating foil.

24. A device for delivering nicotine to a subject, the device comprising a housing comprising:
a body extending along a longitudinal axis, the body defining an airflow inlet and an airflow outlet;
a first tubular compartment extending along the longitudinal axis and comprising an adsorbent element constructed to contain a first liquid;
a second tubular compartment extending along the longitudinal axis in an end-to-end relationship with the first compartment, the second compartment comprising an adsorbent element constructed to contain a second liquid; and
a third tubular compartment adjacent the airflow outlet, extending along the longitudinal axis in an end-to-end relationship with the second compartment,
at least one of the first and second tubular compartments comprising a frangible barrier end cap,
the device comprising a penetration member constructed to penetrate the frangible barrier end cap to form an airflow path between the airflow inlet and the airflow outlet and extending sequentially through the first, second, and third tubular compartments.

* * * * *